US010327655B2

(12) United States Patent
Angle et al.

(10) Patent No.: US 10,327,655 B2
(45) Date of Patent: Jun. 25, 2019

(54) NEURAL-INTERFACE PROBE AND METHODS OF PACKAGING THE SAME

(71) Applicant: Paradromics, Inc., San Jose, CA (US)

(72) Inventors: Matthew R. Angle, San Jose, CA (US); Yifan Kong, San Jose, CA (US)

(73) Assignee: Paradromics, Inc., Austin, TX (US)

( * ) Notice: Subject to any disclaimer, the term of this patent is extended or adjusted under 35 U.S.C. 154(b) by 0 days.

(21) Appl. No.: 15/482,583

(22) Filed: Apr. 7, 2017

(65) Prior Publication Data

US 2017/0290521 A1    Oct. 12, 2017

Related U.S. Application Data

(60) Provisional application No. 62/321,126, filed on Apr. 11, 2016.

(51) Int. Cl.
*A61B 5/04* (2006.01)
*A61B 5/0478* (2006.01)
*A61B 5/00* (2006.01)

(52) U.S. Cl.
CPC ........ *A61B 5/04001* (2013.01); *A61B 5/0478* (2013.01); *A61B 5/4064* (2013.01); *A61B 5/6868* (2013.01); *A61B 2562/0209* (2013.01)

(58) Field of Classification Search
CPC ... A61B 5/04; A61B 5/04001; A61B 5/04002; A61B 5/04004; A61B 5/0404; A61B 5/0408; A61B 5/04082; A61B 5/04085; A61B 5/04087; A61B 5/0416; A61B 5/0476; A61B 5/0478; A61B 5/0482; A61B 5/0484; A61B 5/6868; A61B 5/6877; A61N 1/0526; A61N 1/0529; A61N 1/0531; A61N 1/0534
See application file for complete search history.

(56) References Cited

U.S. PATENT DOCUMENTS 3,982,529 A * 9/1976 Sato .................... A61B 5/0408
   600/392
5,008,733 A * 4/1991 Mine .................... H01L 23/057
   257/702

(Continued)

FOREIGN PATENT DOCUMENTS

EP      2495011 A1    9/2012

OTHER PUBLICATIONS

Bouton, C. et al., Restoring cortical control of functional movement in a human with quadriplegia. Nature, 2016; vol. 000, 13 pages.

(Continued)

*Primary Examiner* — Eun Hwa Kim
(74) *Attorney, Agent, or Firm* — Wilson Sonsini Goodrich & Rosati

(57) ABSTRACT

A neural-interface probe is provided. The probe may comprise a chip, a wire bundle substrate, and an encapsulant material. The chip may comprise a plurality of bond pads. The wire bundle substrate may comprise a plurality of wires extending through the substrate. The plurality of wires may comprise: (1) a proximal portion connected to the plurality of bond pads to thereby couple the chip to the substrate, and (2) a flexible distal portion configured to interface with neural matter. The encapsulant material may be disposed at least between the chip and the wire bundle substrate.

24 Claims, 19 Drawing Sheets

(56) References Cited

U.S. PATENT DOCUMENTS

| | | | |
|---|---|---|---|
| 5,721,450 A * | 2/1998 | Miles | H01L 23/3128 |
| | | | 257/667 |
| 6,049,038 A | 4/2000 | Suzuki | |
| 6,393,327 B1 | 5/2002 | Scribner | |
| 6,647,297 B2 | 11/2003 | Scribner | |
| 6,815,258 B2 | 11/2004 | Vincent | |
| 6,920,359 B2 | 7/2005 | Meadows et al. | |
| 6,940,182 B2 | 9/2005 | Hilton et al. | |
| 7,091,060 B2 | 8/2006 | Bolken et al. | |
| 7,134,198 B2 | 11/2006 | Nakatani et al. | |
| 7,306,976 B2 | 12/2007 | Feustel et al. | |
| 7,991,475 B1 * | 8/2011 | Tang | A61B 5/04001 |
| | | | 600/373 |
| 8,010,208 B2 | 8/2011 | Nimer et al. | |
| 8,024,049 B1 | 9/2011 | Gilson et al. | |
| 8,280,516 B2 | 10/2012 | Graupe | |
| 8,406,889 B2 | 3/2013 | Llinas et al. | |
| 8,412,332 B2 | 4/2013 | Massoud-Ansari et al. | |
| 8,649,873 B2 | 2/2014 | Moffitt et al. | |
| 8,798,737 B2 | 8/2014 | Merz et al. | |
| 8,849,408 B1 | 9/2014 | Gilson et al. | |
| 8,929,992 B2 | 1/2015 | Toader et al. | |
| 8,944,985 B2 | 2/2015 | Bonmassar et al. | |
| 2002/0014688 A1 * | 2/2002 | Ramalingam | H01L 21/563 |
| | | | 257/686 |
| 2004/0006264 A1 | 1/2004 | Mojarradi et al. | |
| 2004/0026792 A1 | 2/2004 | Vincent | |
| 2004/0133118 A1 * | 7/2004 | Llinas | A61B 5/04001 |
| | | | 600/544 |
| 2005/0217796 A1 | 10/2005 | Carter et al. | |
| 2005/0267347 A1 | 12/2005 | Oster | |
| 2006/0206161 A1 | 9/2006 | Nicolelis et al. | |
| 2006/0265039 A1 | 11/2006 | Bartic et al. | |
| 2007/0106143 A1 * | 5/2007 | Flaherty | A61B 5/04001 |
| | | | 600/373 |
| 2007/0142872 A1 | 6/2007 | Mickle et al. | |
| 2008/0170819 A1 * | 7/2008 | Kodama | G02B 6/138 |
| | | | 385/14 |
| 2008/0208283 A1 | 8/2008 | Vetter et al. | |
| 2009/0004471 A1 * | 1/2009 | Amthor | A61B 5/04001 |
| | | | 428/375 |
| 2009/0120216 A1 | 5/2009 | Chiou et al. | |
| 2010/0029148 A1 | 2/2010 | Perlin et al. | |
| 2010/0114272 A1 | 5/2010 | Haidarliu et al. | |
| 2010/0161019 A1 * | 6/2010 | Clark | A61N 1/0556 |
| | | | 607/116 |
| 2011/0208031 A1 | 8/2011 | Wolfe et al. | |
| 2012/0041294 A1 * | 2/2012 | Bai | A61B 5/0478 |
| | | | 600/378 |
| 2012/0109262 A1 | 5/2012 | Martens et al. | |
| 2013/0030500 A1 | 1/2013 | Toader et al. | |
| 2013/0175733 A1 | 7/2013 | De et al. | |
| 2013/0190586 A1 * | 7/2013 | Akingba | A61B 5/04001 |
| | | | 600/372 |
| 2013/0274843 A1 | 10/2013 | Barker et al. | |
| 2014/0107728 A1 | 4/2014 | Fried et al. | |
| 2014/0309548 A1 | 10/2014 | Merz et al. | |
| 2014/0330354 A1 | 11/2014 | Shelton et al. | |
| 2014/0350634 A1 | 11/2014 | Grill et al. | |
| 2015/0065831 A1 | 3/2015 | Popovic et al. | |
| 2016/0128588 A1 * | 5/2016 | Melosh | A61B 5/04001 |
| | | | 600/378 |
| 2016/0302687 A1 * | 10/2016 | Lee | A61B 5/05 |

OTHER PUBLICATIONS

Brenner, W. Use underfill encapsulants to enhance flip-chip assembly reliability. Electronic Design. Jul. 30, 2012; Retrieved Feb. 29, 2016 available at http://electronicdesign.com/boards/useunderfillen capsulantsenhanceflipchipassemblyreliability.

Instruction for use (IFU) Blackrock research assemblies. Blackrock Microsystems, LLC. 2014. pp. 0-13.

Johnson, L.J. et al., A novel high electrode count spike recording array using an 81,920 pixel transimpedance amplifier-based imaging chip. Journal of Neuroscience methods. 205; 2012: 223-232.

Johnson, R. Wayne, Chapter 19: Flip Chip Assembly and underfilling, Auburn University, Available at https://pdfs.semanticscholar.org/3c24/524ef9ede82c95ba10caae142e3ca8b58966.pdf.

Mauron, F. Improvements in glass encapsulation technology offer significant advantages for implantable medical devices. Valtronic. p. 1-10.

Scribner, D. et al., A retinal prosthesis technology based on CMOS microelectronics and microwire glass electrodes. IEEE transactions on biomedical circuits and systems, 1(1); Mar. 2007: p. 73-84.

International Search Report dated Jun. 19, 2017 for International Application No. PCT/US2017/026707.

Angle et al. Neuronal Recordings with Solid-Conductor Intracellular Nanoelectrodes (SCINEs). PLOS One 7(8):E43194 (Aug. 2012). 8 pages.

Hajjhassan et al. NeuroMEMS: Neural Probe Microtechnologies. Sensors 8(10):6704-6726 (Oct. 25, 2008). doi: https://doi.org/10.3390/s8106704.

\* cited by examiner

Part A

Part B

Part A

Part B

Part C

Part D

Part A

Part B

Part C

Part D

NEURAL-INTERFACE PROBE AND METHODS OF PACKAGING THE SAME

CROSS-REFERENCE

This application claims the benefit of U.S. Provisional Application No. 62/321,126 filed Apr. 11, 2016, which is incorporated herein by reference in its entirety.

STATEMENT AS TO FEDERALLY SPONSORED RESEARCH AND DEVELOPMENT

This invention was made with Government support under contracts MH110287 and NS094248 awarded by the National Institutes of Health. The Government has certain rights in the invention.

BACKGROUND OF THE INVENTION

Neural-interface probes may be used to obtain a better understanding of brain functionality, which can lead to improved treatment of certain neurological diseases. Such probes are typically implanted into a brain to record neuronal electrical activity. The neuronal recordings may be analyzed to determine how neural circuits process information at a cellular level.

A neural-interface probe may comprise a high density microelectrode array bonded to a chip. The bonding process may include forming a large number of fine pitch interconnects between the microelectrode arrays and the chip. However, the bonding process may pose certain packaging challenges in terms of alignment precision and interconnect formation, yield, and/or reliability. There is also a need to provide robust packaging for the probe, to prevent thermo-mechanically induced failures such as interconnect cracking/shearing, electrical opens, and/or chip delamination when the probe experiences bending forces and temperature changes during operation. A robust package can also protect the probe from chemical corrosion, while being biocompatible.

SUMMARY OF THE INVENTION

The present invention addresses at least the needs by providing robust packaging structures and assembly methods for a neural-interface probe. The neural-interface probe may be implantable on or into a human brain.

In one aspect of the invention, a neural-interface probe is provided. The probe may comprise a chip, a wire bundle substrate, and an encapsulant material. The chip may comprise a plurality of bond pads. The wire bundle substrate may comprise a plurality of wires extending through the substrate. The plurality of wires may comprise: (1) a proximal portion connected to the plurality of bond pads to thereby couple the chip to the substrate, and (2) a flexible distal portion configured to interface with neural matter. The encapsulant material may be disposed at least between the chip and the wire bundle substrate.

In some embodiments, the proximal portion of the wires may extend from a first surface of the substrate, and the distal portion of the wires may extend from a second surface of the substrate that is different from the first surface. The first surface and the second surface may be laterally opposite to each other. Optionally, the first surface and the second surface may be substantially parallel to each other. Alternatively, the first surface and the second surface may be substantially orthogonal to each other. In some cases, the first surface and the second surface may be oblique to each other.

In some embodiments, the flexible distal portion of the wires may be configured to substantially conform to a surface of the neural matter when the distal portion is in contact with the surface of the neural matter. The flexible distal portion of the wires may be configured to bend when the distal portion is in contact with the surface of the neural matter. In some cases, the surface of the neural matter may have an irregular shape. The flexible distal portion of the wires may be configured to partially penetrate or impinge on the surface of the neural matter.

In some embodiments, the plurality of wires may have a high aspect ratio in a longitudinal direction extending through the substrate. In some cases, the aspect ratio may be greater than 500:1.

The proximal portion of the plurality of wires may be connected to the plurality of bond pads via a plurality of interconnects formed between the chip and the substrate. In some embodiments, the plurality of interconnects may comprise a solder. The solder may be disposed between the proximal portion of the plurality of wires and the plurality of bond pads. The plurality of interconnects may be formed by melting the solder to mechanically join the plurality of wires and the plurality of bond pads. The plurality of interconnects may be configured to electrically connect the plurality of wires to the chip. The plurality of interconnects may be formed by aligning and joining the proximal portion of the plurality of wires to the plurality of bond pads. In some cases, the plurality of interconnects may be formed by aligning the proximal portion of the plurality of wires to the plurality of bond pads to a precision within 10 μm. The solder may be a low melting point metal or metallic alloy.

In some embodiments, an encapsulant material may be an underfill disposed between the chip and the substrate. The encapsulant material may also be an underfill surrounding the plurality of interconnects. In some cases, the encapsulant material may be disposed encapsulating the chip. In some further embodiments, the encapsulant material may form a housing around the chip and the substrate. The flexible distal portion of the plurality of wires may extend outside of the housing, and the proximal portion of the plurality of wires may be disposed within the housing. In some cases, the housing may be configured to hermetically seal the chip and the substrate. The housing may also be configured to provide structural rigidity to the probe along a longitudinal direction that is substantially parallel to the plurality of wires.

In some embodiments, the wire bundle substrate may comprise a bulk portion of the plurality of wires embedded in an epoxy or resin or other organic or polymeric material. The bulk portion of the plurality of wires may be supported by the epoxy material. The flexible distal portion of the plurality of wires may extend outside of the epoxy material. The proximal portion of the plurality of wires may also optionally extend outside of the epoxy material. The proximal portion of the plurality of wires may be located at or near a surface of the epoxy material.

In some embodiments, a length of the bulk portion of the wires may be greater than a length of the flexible distal portion of the wires. Alternatively, a length of the bulk portion of the wires may be substantially equal to or less than a length of the flexible distal portion of the wires.

In some embodiments, the plurality of wires may be randomly distributed at different pitches in the substrate. Alternatively, the plurality of wires may be uniformly distributed at a same pitch in the substrate. In some embodiments, the proximal portion of one or more wires may be connected to a bond pad. Alternatively, the proximal portion of each wire may be connected to each bond pad.

In some embodiments, the chip may be rigidly coupled to the substrate via the plurality of interconnects and the encapsulant material. For example, the chip may not be detachable from the substrate without damaging or breaking one or more of the interconnects. In some other embodiments, the chip may be detachably coupled to the substrate via the plurality of interconnects. For example, the plurality of interconnects may include solder interconnects that can be melted to allow the chip to be decoupled from the substrate, prior to application of the encapsulant material.

In some embodiments, the flexible distal portion of the wires may be configured to spread out in a plurality of different directions in a three-dimensional configuration. Each of the plurality of wires may comprise a conductive core surrounded by an insulating layer. A material of the insulating layer may be different from the epoxy material. In some cases, a portion of the insulating layers at the proximal portion of the wires may be etched back or otherwise controllably removed to expose a first end of the conductive cores. In some cases, a portion of the insulating layers at the distal portion of the wires may be etched back to expose a second end of the conductive cores. In some cases, a length of the exposed second end of the conductive cores may be greater than a length of the exposed first end of the conductive cores.

In some embodiments, a length of the probe may range from about 1 mm to about 8 cm. Alternatively, a length of the probe may be less than 1 mm or greater than 8 cm. A diameter of each of the plurality of wires may range from about 5 µm to about 25 µm. A length of the flexible distal portion of the wires may range from about 2 mm to about 4 cm.

In another aspect of the invention, a method for forming a neural-interface probe is provided. The method may comprise providing a chip that comprises a plurality of bond pads; providing a wire bundle substrate that comprises a plurality of wires extending through the substrate, wherein the plurality of wires comprise: (1) a proximal portion configured to be connected to the plurality of bond pads to thereby couple the chip to the substrate, and (2) a flexible distal portion configured to interface with neural matter; attaching the chip to the wire bundle substrate by connecting the proximal portion of the wires to the plurality of bond pads; and providing an encapsulant material at least between the chip and the wire bundle substrate.

In some embodiments, the method may further comprise: positioning the flexible distal portion of the wires in contact with a surface of the neural matter, such that the distal portion substantially conforms to the surface of the neural matter. The flexible distal portion of the wires may be configured to bend when said distal portion is in contact with the surface of the neural matter. In some embodiments, the method may further comprise: effecting the flexible distal portion of the wires to partially penetrate or impinge on the surface of the neural matter. In some embodiments, connecting the proximal portion of the wires to the plurality of bond pads may comprise forming a plurality of interconnects between the chip and wire bundle substrate. The plurality of interconnects may comprise a solder. Forming the plurality of interconnects may comprise melting the solder to mechanically join the plurality of wires and the plurality of bond pads. Connecting the proximal portion of the wires to the plurality of bond pads may comprise aligning and joining the proximal portion of the plurality of wires to the plurality of bond pads. In some cases, the proximal portion of the plurality of wires may be aligned to the plurality of bond pads to a precision within 10 µm.

In some embodiments, the encapsulant material may be an underfill disposed between the chip and the substrate. The encapsulant material may be an underfill surrounding the plurality of interconnects. In some embodiments, the method may further comprise encapsulating the chip using the encapsulant material. In some further embodiments, the method may further comprise forming a housing around the chip and the substrate using the encapsulant material.

In some embodiments, the flexible distal portion of the plurality of wires may extend outside of the housing, and the proximal portion of the plurality of wires may be disposed within the housing. In some cases, the method may further comprise hermetically sealing the chip and the substrate via the housing. In some cases, the method may further comprise forming the wire bundle substrate by embedding the plurality of wires in an epoxy material.

In some embodiments, connecting the proximal portion of the wires to the plurality of bond pads may comprise connecting the proximal portion of one or more wires to a bond pad. In other embodiments, connecting the proximal portion of the wires to the plurality of bond pads may comprise connecting the proximal portion of each wire to each bond pad.

In a further aspect of the invention, a method for monitoring and/or stimulating neural activity is provided. The method may comprise inserting a neural-interface probe of any of the foregoing embodiments into a brain, such that the flexible distal portion of the wires interfaces and is in contact with an area of the neural matter; and monitoring and/or stimulating neural activity in the area via a plurality of electrical signals transmitted between the chip and the neural matter.

In some embodiments, the plurality of electrical signals may be transmitted through the plurality of wires. In some cases, the method may further comprise transmitting the electrical signals from the probe to an external monitoring device via one or more wireless or wired communication channels.

Additional aspects and advantages of the present disclosure will become readily apparent to those skilled in this art from the following detailed description, wherein only exemplary embodiments of the present disclosure are shown and described, simply by way of illustration of the different modes contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
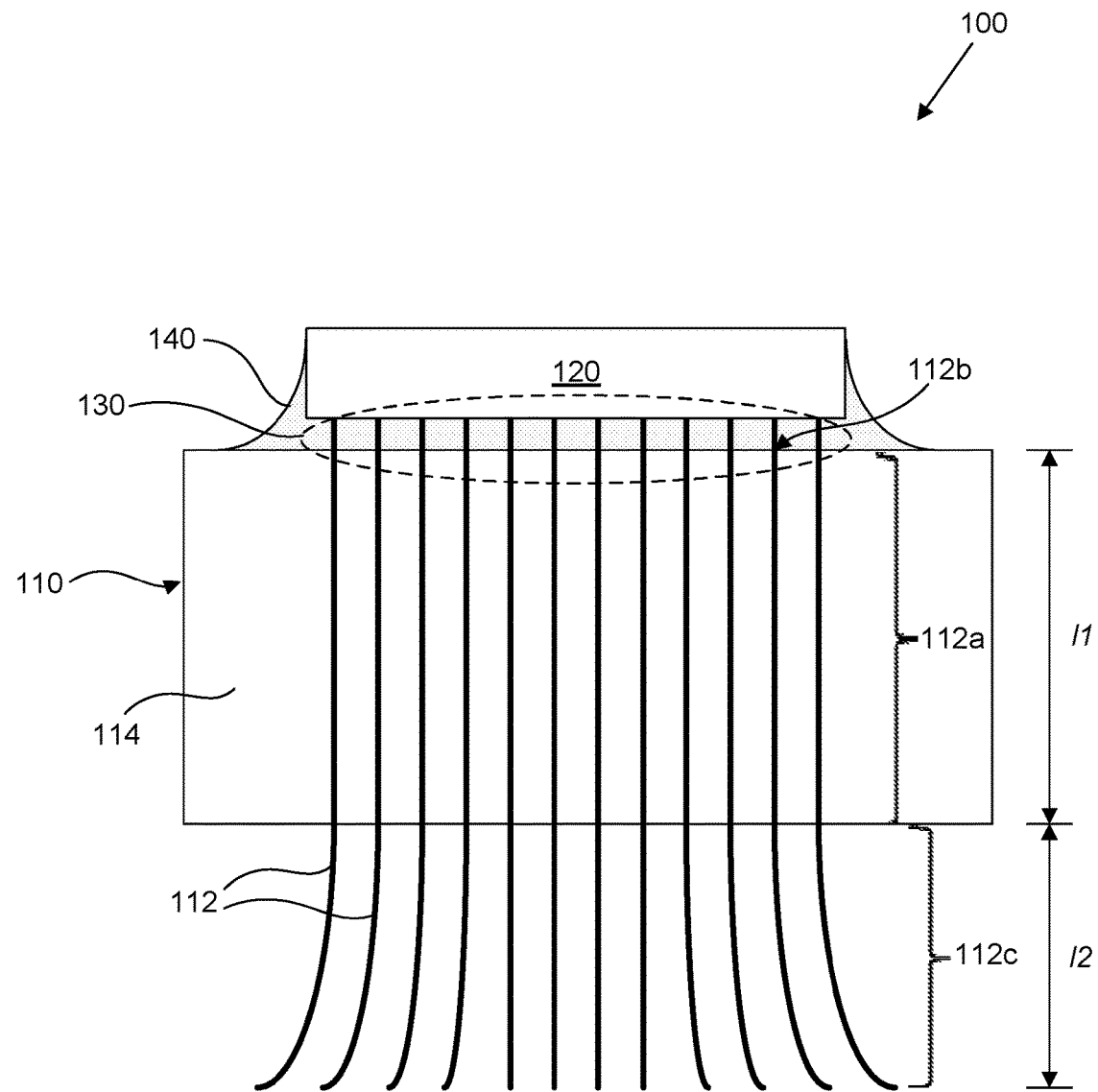
FIG. 1A depicts a schematic of a neural-interface probe in accordance with some embodiments.

Embodiments of the invention are directed to a neural-interface probe comprising a wire bundle having a plurality of wires configured to interface with neural matter. The wires in the wire bundle are configured to be electrically interconnected with a chip. The chip may be configured to stimulate and/or monitor brain activity. In some instances, the chip may be an integrated circuit imaging chip capable of recording neural signals from areas and/or curved surfaces within a brain. In some cases, the wires of the wire bundle may be individually addressable, such that one or more wires can be configured to provide multi-site, spatially controlled stimulation of neural matter. For example, the chip may comprise a plurality of pixels controlling a plurality of electrodes. One or more wires of the wire bundle may be connected to each pixel. The stimulation frequency and amplitude of each electrode can be individually fine-tuned to control the pixels.

FIG. 1 depicts a schematic of a neural-interface probe in accordance with some embodiments. A neural-interface probe 100 may comprise a wire bundle substrate 110 and a chip 120. The wire bundle substrate and the chip may be electrically and mechanically coupled to each other via a plurality of interconnects 130. The neural-interface probe may further comprise an underfill 140 disposed between the wire bundle substrate and the chip. The underfill 140 may be an encapsulant material that surrounds the plurality of interconnects.

The wire bundle substrate may comprise one or more wires 112 extending through the substrate. The wires may be configured to transmit electrical signals between the chip and neural matter within a brain. In the example of FIG. 1, the wire bundle substrate may comprise n number of wires, where n may be any integer greater than 1. For example, the wire bundle substrate may comprise 100, 1000, 10000, or 1000000 wires, fewer than 100 wires, greater than 1000000 wires, or any number between the aforementioned ranges. In some embodiments, the wire bundle substrate may include at least one optical fiber (not shown) in addition to wires 112. The optical fiber may be configured to transmit light signals that enable imaging of the neural matter into which the probe 100 is inserted.

The wires 112 may be held together by a support base 114. As shown in FIG. 1, a bulk portion 112a of the wires 112 may be embedded within the support base. The bulk portion 112a of the wires may have any shape (e.g., circular, triangular, quadrilateral, etc.) as viewed from the top of the wire bundle substrate. The bulk portion 112a of the wires may have substantially fixed positions since the bulk portion is physically constrained by the support base. The support base may be made of a rigid material. The support base may be made of an insulating material or dielectric. In some embodiments, the support base may be made of an epoxy or resin material. Materials suitable for use as the support base may include silicone compounds (e.g., polydimethylsiloxane (PDMS), poly(methyl methacrylate) (PMMA), etc.), medical-grade epoxies, organic polymer encapsulants, composite materials, and the like. In some embodiments, the support base may be made of glass.

The opposite ends of the wires may correspond to a proximal portion 112b and a distal portion 112c. The proximal portion 112b of the wires may be configured to be mechanically/electrically connected to the chip, as described in detail later in the specification. For example, the proximal portion 112b of the wires may be connected to a plurality of bond pads on the chip 120, to thereby bond the chip to the substrate.

The proximal portion of the wires may extend from a first surface of the substrate, and the distal portion of the wires may extend from a second surface of the substrate that is different from the first surface. In some cases, the first surface and the second surface may correspond respectively to a top surface and a bottom surface of the substrate. The first surface and the second surface may be laterally opposite to each other. Additionally, the first surface and the second surface may be substantially parallel to each other. In some cases, the first surface and the second surface may be substantially orthogonal to each other. Alternatively, the first surface and the second surface are oblique to each other. Any spatial arrangement of the first surface relative to the second surface may be contemplated.

The distal portion 112c may correspond to a freely extending portion of the wires. The distal portion of the wires may be configured to interface with a region of the brain. A length l2 of the distal portion of the wires may be configured such that the distal portion of the wires is capable of interfacing with neural matter within the brain. The distal portion of the wires may be relatively unrestrained, and can move relative to one another even though the bulk portion of the wires is rigidly held by the support base. The distal portion of the wires may be flexible and configured to interface with neural matter. The distal portion of the wires may be capable of moving laterally relative to one another upon application of an external force. For example, the distal portion of the wires may be capable of conforming to or bending when pressed against neural matter. A rigidity of the distal portion of the wires may depend on the length l2 of the distal portion, akin to a "cantilever effect" whereby the distal portion of the wires is cantilevered from the base support. For example, the rigidity of the distal portion of the wires may increase as l2 decreases, such that the distal portion experiences a higher restraint (e.g., the free end of the wires splay out over a smaller area). Conversely, the rigidity of the distal portion of the wires may decrease as l2 increases, such that the distal portion experiences a lower restraint (e.g., the free end of the wires splay out over a larger area). The distal portion of the wires may be configured to spread out in a plurality of different directions in a three-dimensional configuration.

The distal portion 112c of the wires may be configured to substantially conform to a surface of the neural matter when the distal portion of the wires is in contact with the surface of the neural matter. In some cases, the distal portion of the wires may be configured to bend when the distal portion of the wires is in contact with the surface of the neural matter. The surface of the neural matter may have an irregular shape (or alternatively, a regular shape). In some cases, the distal portion of the wires may be configured to impinge on and/or partially penetrate the surface of the neural matter. In some other embodiments, the distal portion of the wires may be configured to remain rigid, such that the distal portion of the wires does not yield upon contact with or insertion into the neural matter. This results in the distal portion of the wires maintaining the same structural disposition pre-insertion as well as post-insertion into the neural matter.

A length of the bulk portion 112a of the wires may be given by l1. A ratio of the lengths of the bulk portion and the distal portion of the wires may be given by l1:l2. In some embodiments, the ratio l1:l2 may be 1:1, 2:1, 3:1, 4:1, 5:1, 6:1, 7:1, 8:1, 9:1, 10:1, or greater than 10:1. Alternatively, in other embodiments, the ratio l1:l2 may be 1:1, 1:2, 1:3, 1:4, 1:5, 1:6, 1:7, 1:8, 1:9, 1:10, or greater than 1:10. Any ratio of l1:l2 may be contemplated. The ratio of l1:l2 may be configured such that the support base provides adequate mechanical strength over a length of the probe that is suitable for enabling insertion of the probe into a brain. At the same time, the ratio of l1:l2 may be configured such that the distal portion of the wires is capable of interfacing with a desired size of the brain area, and sampling the area with a desired sampling density. In some cases, the plurality of wires may have a high aspect ratio in a longitudinal direction extending through the substrate. For example, the aspect ratio may be 100:1, 200:1, 300:1, 400:1, 500:1, 600:1, 700:1, 800:1, 900:1, 1000:1, or greater than 1000:1. Any aspect ratio may be contemplated and designed for, depending on the length of wire needed to reach different parts of the brain (e.g., deep brain regions or superficial brain regions) for different neural applications/stimulations. In some embodiments, the length l2 of the distal portion of the wires may range from about 2 mm to about 4 cm.

Figure 2:
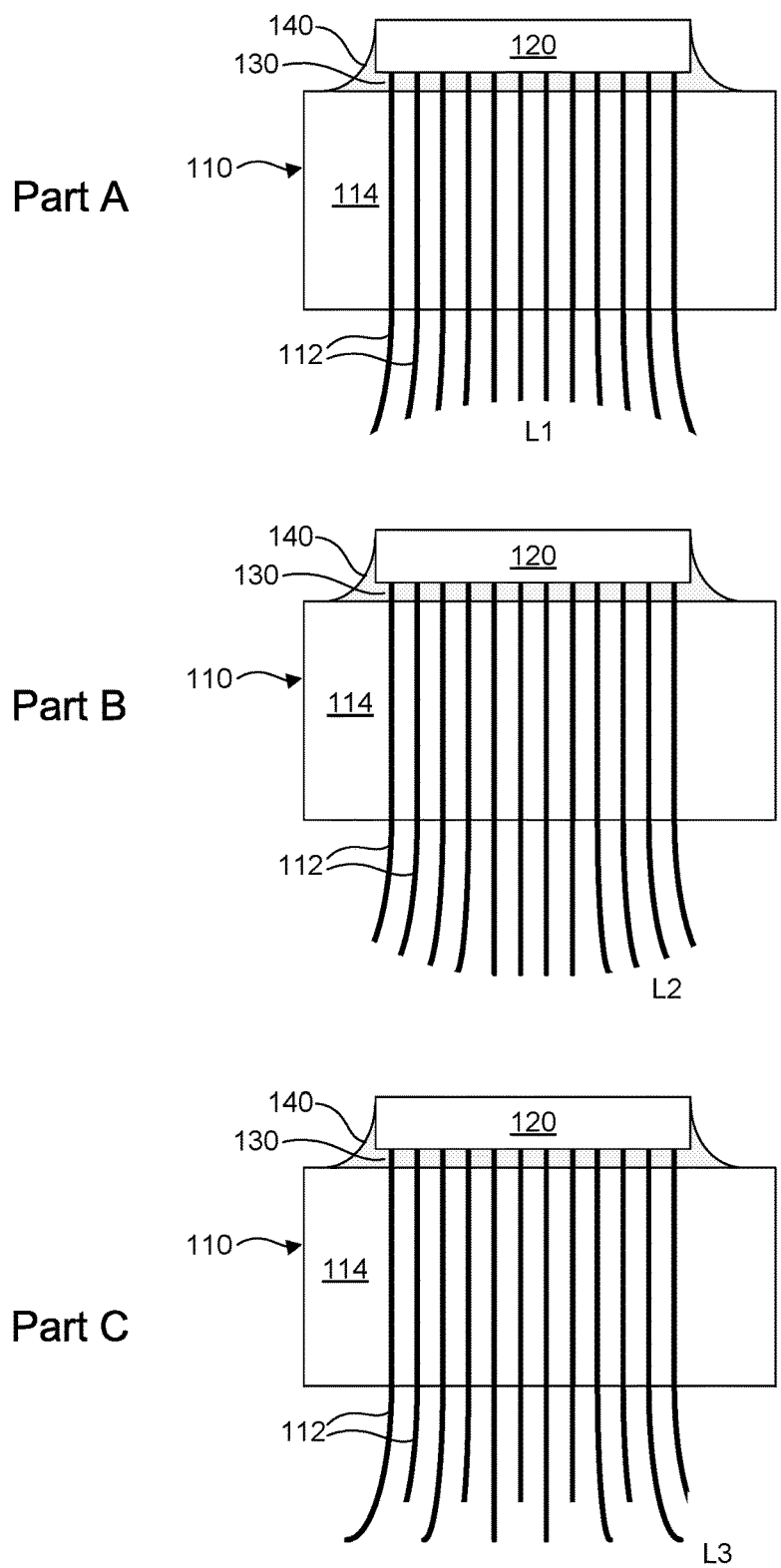
FIG. 2 Parts A, B and C shows examples of the distal portion of the wires having different length configurations.

The length(s) of the distal portion 112c of the wires may or may not be uniform. FIG. 2 shows examples of the distal portion of the wires having different length configurations. In part A, the distal portion of the wires may have a first length configuration L1, such that the distal portion forms a concave shape. In part B, the distal portion of the wires may have a second length configuration L2, such that the distal portion forms a convex shape. In part C, the distal portion of the wires may have a third length configuration L3, such that the distal portion has alternating staggered lengths. The length of the distal portion of the wires may be staggered to reduce instantaneous pressure during insertion into neural tissue. A cortical layer may have an amorphous shape or profile, and it may be difficult to accurately target the depth of the cortical layer. The staggered lengths can ensure that a greater volume/area of neural tissue is sampled since the staggered lengths may more closely conform to the amorphous shape/profile of the cortical layer. In some cases, the staggered lengths can contact or penetrate into multiple cortical layers, thus allowing data to be recorded from distinct and separate cortical layers. The distal portion of the wires may be formed having any shape and/or distribution (e.g., circular concave, circular convex, pyramidal, conical, hemispherical, etc.), which can provide advanced recording and/or stimulation of neural activity.

Figure 1B:
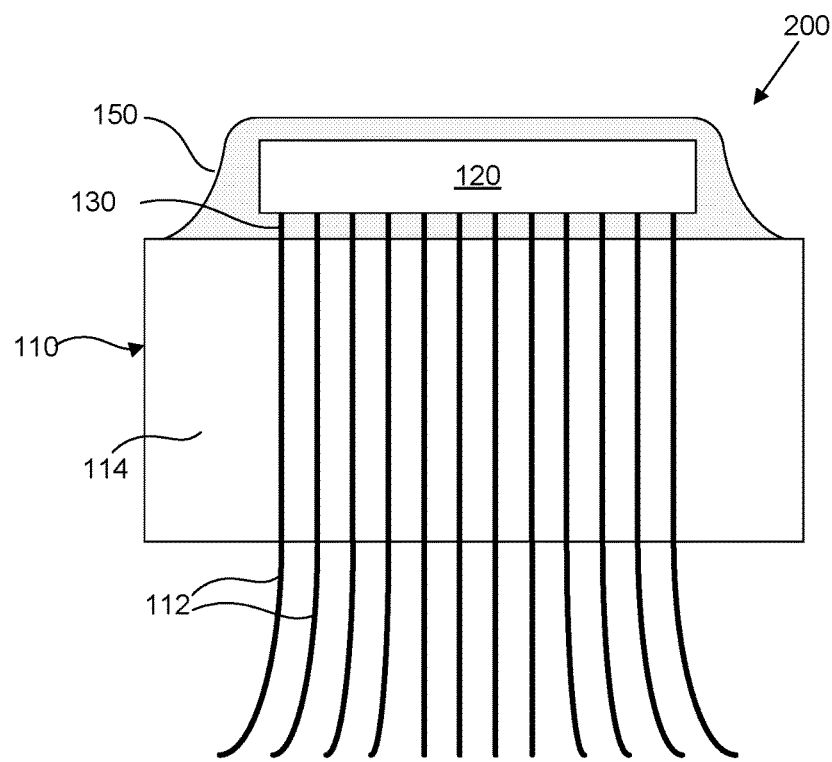
FIGS. 1B and 1C depict schematics of neural-interface probes in accordance with some other embodiments.
Figure 1C:
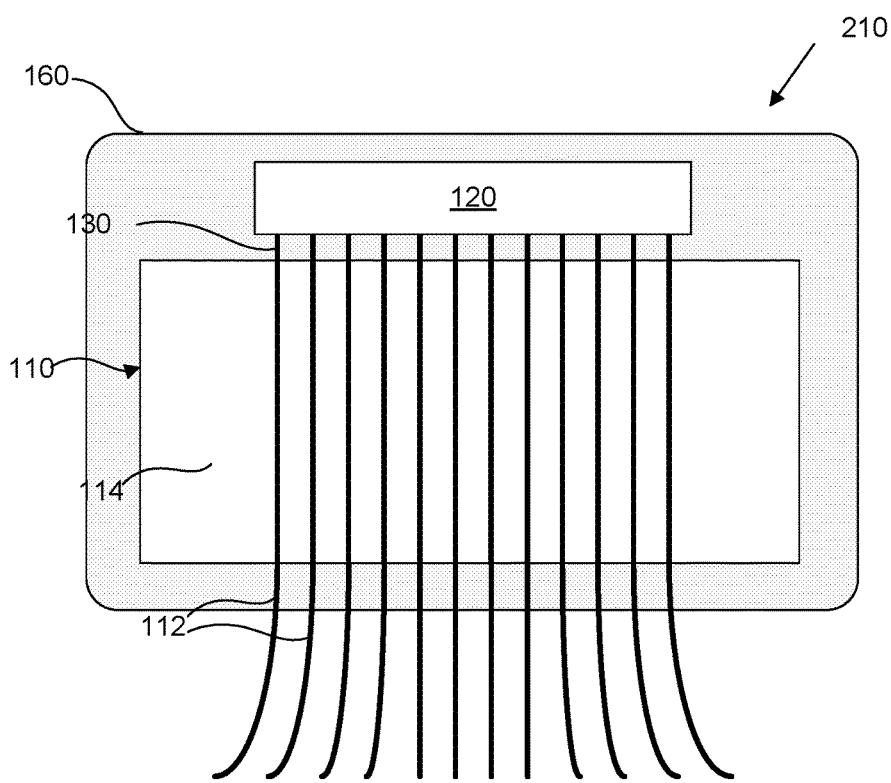

FIGS. 1B and 1C depict schematics of neural-interface probes in accordance with some other embodiments. Specifically, FIGS. 1B and 1C illustrate the use of additional packaging materials to reinforce the neural-interface probe shown in FIG. 1A. In neural-interface probe 200 of FIG. 1B, an encapsulating material may be dispensed on the surrounding areas on the chip and the wire bundle substrate to form an encapsulation layer 150. The encapsulation layer may serve to further protect the regions surrounding the chip. In some cases, an underfill may be omitted and the encapsulating material may be dispensed into the gap between the chip and wire bundle substrate (i.e., the encapsulating material may also serve as an underfill). In some other embodiments, the assembly in FIG. 1B may undergo an overmolding process to form a housing 160 sealing the chip and the substrate, while leaving the distal portion of the wires freely extending, for example as shown by neural-interface probe 210 of FIG. 1C. The materials used in the encapsulation layer and the housing may be biocompatible. In some cases, the housing 160 may be formed by overmolding an epoxy block around the chip and the substrate, and subsequently grinding/polishing/machining the epoxy block into a desired shape for the housing. In some embodiments, the distal portion of the wires may be initially embedded in the epoxy block, and the epoxy block is then etched to expose the distal portion of the wires. It should be noted that the housing may be formed having any shape (for example, cubic, spherical, cylindrical, trapezoidal, etc.).

In the examples of FIGS. 1A, 1B, and 1C, the chip may be rigidly coupled to the substrate via the plurality of interconnects and an encapsulant material (e.g., underfill, encapsulation layer, and/or housing). Accordingly, the chip may not be detachable from the substrate without damaging or breaking one or more of the interconnects. In some other embodiments, the chip may be detachably coupled to the substrate via the plurality of interconnects. For example, the plurality of interconnects may include solder interconnects that can be melted to allow the chip to be decoupled from the substrate, prior to application of the encapsulant material.

Figure 3:
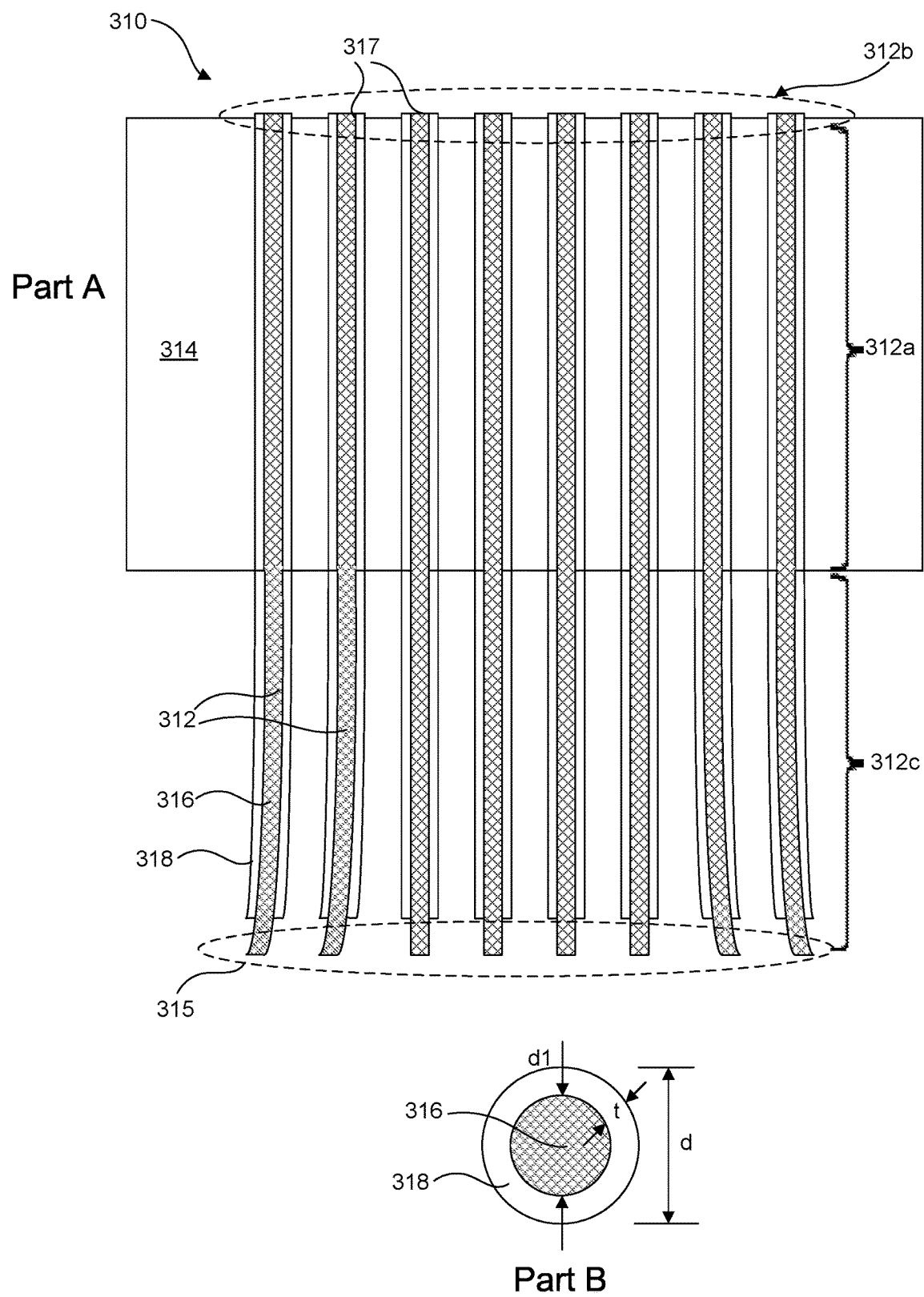
FIG. 3 Parts A and B illustrate a wire bundle substrate in accordance with some embodiments.

FIG. 3 shows a wire bundle substrate in accordance with some embodiments. The wire bundle substrate in FIG. 3 may, for example correspond to the wire bundle substrate in FIG. 1. In the example of FIG. 3, a wire bundle substrate 310 may comprise a plurality of wires 312. The wires may be configured to transmit electrical signals between the chip and neural matter. The wires may be held together by a support base 314. A bulk portion 312a of the wires may be embedded within the support base. The ends of the wires may comprise a proximal portion 312b and a distal portion 312c. The proximal portion 312b may be configured to be mechanically/electrically connected or coupled to a chip (e.g., chip 120 in FIG. 1). The distal portion 312c may correspond to a freely extending portion of the wires.

Each of the wires 312 may comprise a conductive core 316 surrounded by an insulating layer 318. The conductive core and/or the insulating layer may be made of any appropriate material that is biocompatible and suitable for insertion into neural matter. The conductive core may be made of a metal (e.g., gold, copper, platinum, silver, etc.) or any metallic alloy. In some embodiments, the conductive core may be made of a semiconductor, a conductive polymer, or a conductive composite material. The wires 312 may be formed by a thermal drawing process, for example by drawing glass as a cladding over the conductive core. Accordingly, the insulating layer 318 may be made of glass. The insulating layer may also be made of other insulating materials such as silicone compounds (e.g., polydimethylsiloxane (PDMS), poly(methyl methacrylate) (PMMA), etc.), medical-grade epoxies, organic polymer encapsulants, composite materials, and the like. In some embodiments, the insulating layer 318 may comprise a plurality of insulating layers having one or more different material properties (e.g., dielectric constant, chemical reactivity/resistance, hardness, etc.). In some embodiments, the insulating layer 318 and a base support (e.g., base support 114) for holding the bulk portion of the wires may be made of different materials.

Referring to part B of FIG. 3, each of the wires 312 may have a diameter d which is determined by a diameter d1 of the conductive core 316 and a thickness t of the insulating layer 318. The diameter of each wire may be given by d=d1+2t. In some embodiments, the diameter d1 of the conductive core may be 1 μm, 2 μm, 3 μm, 4 μm, 5 μm, 6 μm, 7 μm, 8 μm, 9 μm, or 10 μm. Optionally, the diameter d1 of the conductive core may be less than 1 μm, or greater than 10 μm. In some embodiments, the thickness t of the insulating layer may be 1 μm, 2 μm, 3 μm, 4 μm, 5 μm, 6 μm, 7 μm, 8 μm, 9 μm, or 10 μm. Optionally, the thickness t of the insulating layer may be less than 1 μm, or greater than 10 μm. Any values for d, d1, and t may be contemplated. In some embodiments, the diameter d may range from about 5 μm to about 25 μm.

In some embodiments, the plurality of wires 312 may have different diameters. For example, the wires may comprise a first set of wires having a first diameter and a second set of wires having a second diameter. The first and second diameters may be different. The different wire diameters may be obtained by adjusting the diameters of the conductive cores and/or the thicknesses of the insulating layers respectively for the first and second sets of wires.

The conductive cores 316 may be exposed at the tip of the distal portion 312c of the wires. In some embodiments, a portion of the insulating layer 318 at the tip of the distal portion may be etched to further expose the conductive cores. The exposed portions of the conductive cores at the tip of the distal portion may correspond to electrodes 315 (shown in part C of FIG. 3). The electrodes 315 may be configured to interface with neural matter within a brain. In some embodiments, the electrodes 315 may be electrochemically coated with a low-impedance coating, such as iridium oxide (or other transition-metal oxide, such as $MnO_2$, etc.), a conductive polymer (e.g., PEDOT, etc.), or a material promoting a high surface area (e.g. carbon nanotubes, platinum black, nanoparticle composites, and the like). The surface modification can decrease the interfacial electrical impedance between the exposed conductor core and brain tissue, thereby increasing the sensitivity of the neural-activity recording.

In some embodiments, it may be desirable to remove a portion of the base support to increase the length l2 of the distal portion of the wires. In those embodiments, the base support 314 and the insulating layer 318 may be made of different materials that are capable of being etched by different reactants. Alternatively, the base support 314 and the insulating layer 318 may be made of different materials that are capable of being etched by a same reactant but at different etch rates. For example, to increase the length l2 of the distal portion of the wires, a bottom portion of the base support 314 may be etched using a reactant that has a higher etch selectivity with respect to the base support (i.e., the base support is etched faster than the insulating layer at the distal portion). In some embodiments, a reactant's etch selectivity of the base support to the insulating layer may be 2:1, 3:1, 4:1, 5:1, 6:1, 7:1, 8:1, 9:1, 10:1, or greater than 10:1. Any ratio of the etch selectivity may be contemplated, and different reactants with different etch selectivities may be used. For example, in some embodiments, a first reactant with a higher etch selectivity may be initially used to remove material in bulk from the base support, followed by a second reactant with a lower etch selectivity for fine removal of material and to smoothen the end surfaces of the base support and the insulating layer. In some other embodiments, the base support may be etched by a reactant that has no or little etching effect on the insulating layer.

Figure 4:
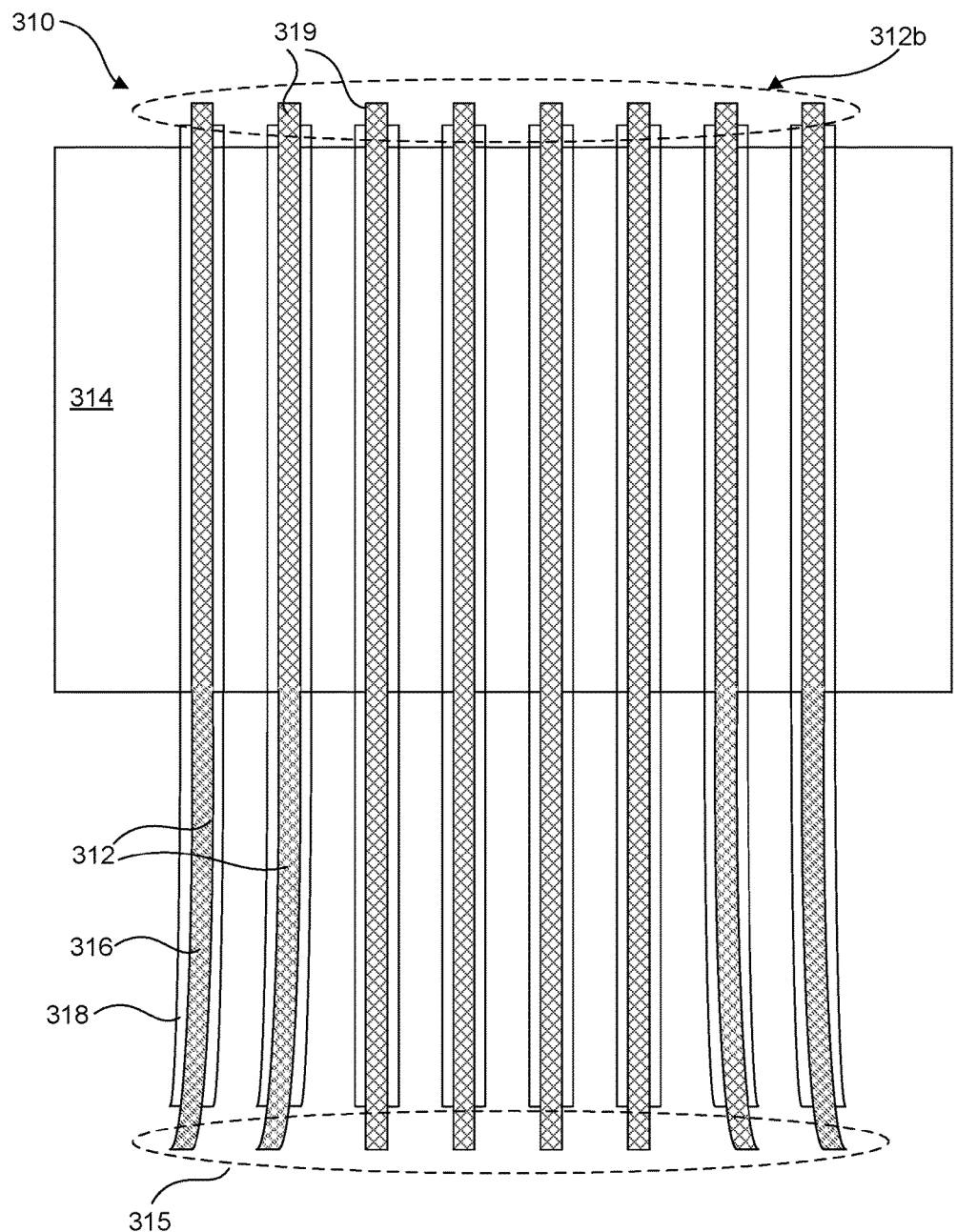
FIG. 4 shows an example in which a portion of the insulating layers of the wires is etched to further expose the conductive cores of the wires, in accordance with some embodiments.

The conductive cores 316 may also be exposed at the proximal portion 312b of the wires. The exposed portion of the conductive cores at the proximal portion may correspond to connection pads 317. In some embodiments, a portion of the insulating layer 318 at the tip of the proximal portion may be etched to further expose the conductive cores, for example as shown in FIG. 4. The exposed portions of the conductive cores at the tip of the proximal end may correspond to substrate wire bumps 319. The wire bundle substrate may be configured to be attached (mechanically and electrically connected) to the chip via the connection pads 317 and/or the substrate wire bumps 319, as described later in the specification.

The substrate wire bumps 319 may be spaced apart by a variable pitch. When the bulk portion of the wires is unevenly distributed within the base support, the substrate wire bumps 319 may be spaced apart by a variable pitch, for example as shown in part A of FIG. 5. In some embodiments, the variable pitch may range from 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, or greater than 20 μm. In some instances, adjacent substrate wire bumps may be in contact with each other.

In some embodiments, the plurality of wires may be coated with a polymer, e.g. a thermoplastic polymer coating. The polymer coating may serve as the encapsulant material. For example, the polymer coating can be melted or molded after the bundle of wires has been formed, which allows the liquid polymer to flow into the gaps between the wires via capillary action to create a hermetic seal. In some cases, a vacuum can be applied to drive excess gas out of the liquid polymer to eliminate bubbles from the seal that may cause reliability issues. In some embodiments, a controlled heating profile may be used to gradually and sequentially melt the polymer from one end of the substrate to the other end of the substrate, in order to avoid/reduce encapsulation of gases as the polymer fills the gaps between the wires via capillary action. This controlled heating profile can be implemented using a conveyor-type convection oven or a hotplate customized with different heating zones. The controlled heating profile can also be carried out in a vacuum to avoid/reduce formation of voids, as described above. In some embodiments, the polymer may include a plurality of layers made of materials having different melting points. In those embodiments, a heating profile comprising a plurality of temperature ramp steps may be used to sequentially melt the different layers to form the hermetic seal.

In some embodiments, the substrate wire bumps 319 may be spaced apart by a constant pitch. For example, when the bulk portion of the wires is uniformly distributed within the base support, the substrate wire bumps 319 may be spaced apart by a substantially constant pitch (e.g., shown in parts B, C, D, and E of FIG. 5). In some embodiments, the constant pitch may be 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, or greater than 20 μm. In some instances, the substrate wire bumps 319 may comprise different sets of wire bumps having constant and/or variable pitches. For example, a first set of wire bumps may be spaced apart at a variable pitch, whereas a second set of wire bumps may be spaced apart at a substantially constant pitch.

Figure 5:
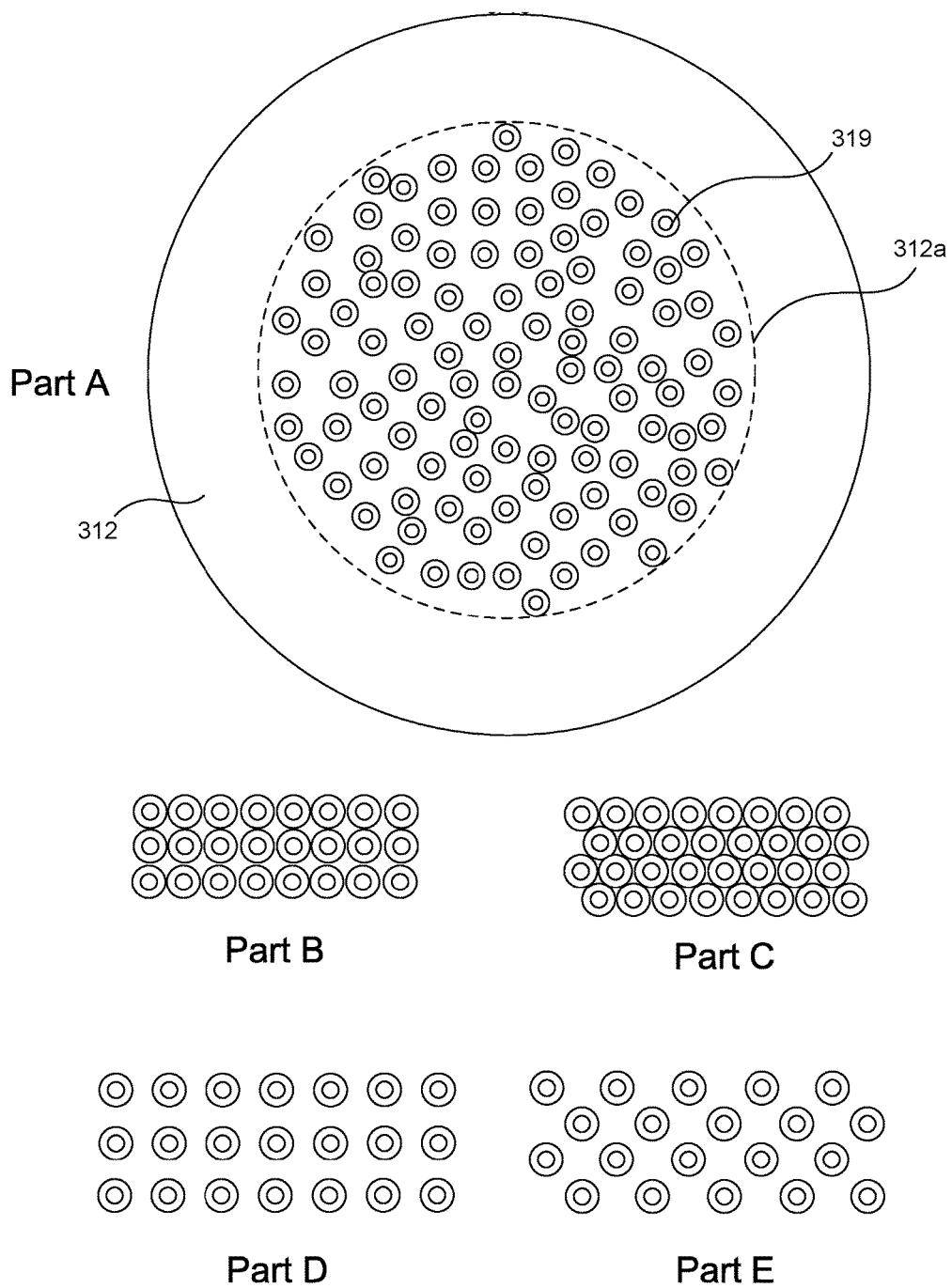
FIG. 5 Parts A, B, C, D and E show examples of the substrate wire bumps having variable and/or constant pitches, in accordance with some embodiments.

Parts B, C, and D of FIG. 5 illustrate different uniform arrays of substrate wire bumps. In parts B and C, the insulating layers for adjacent bumps may be in contact with each other, and the substrate wire bumps are more closely spaced together (i.e., the bulk portion of the wires is packed more densely within the base support). In contrast, the substrate wire bumps in parts D and E are spaced further apart (i.e., the bulk portion of the wires is packed less densely within the base support).

Figure 6:
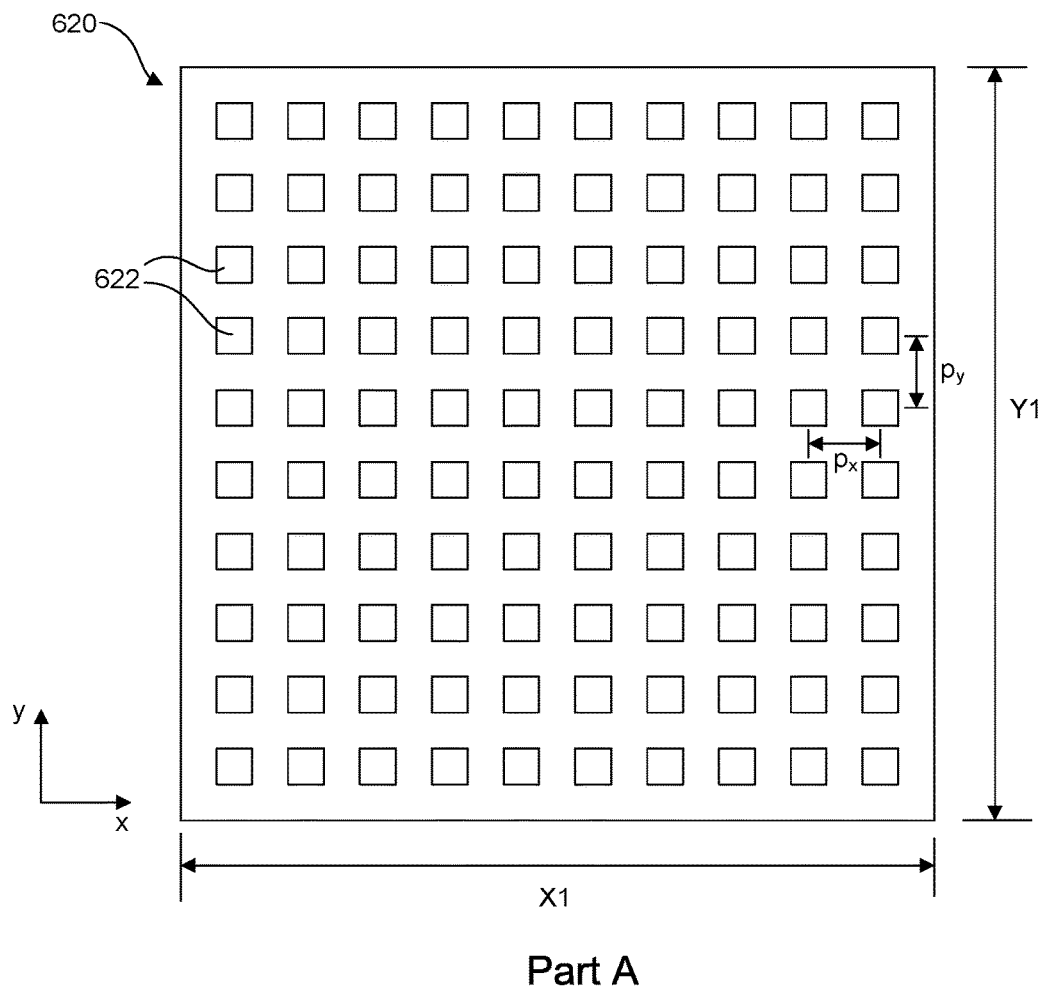
FIG. 6 Parts A and B depict different schematic views of a chip, in accordance with some embodiments.
Figure 6:
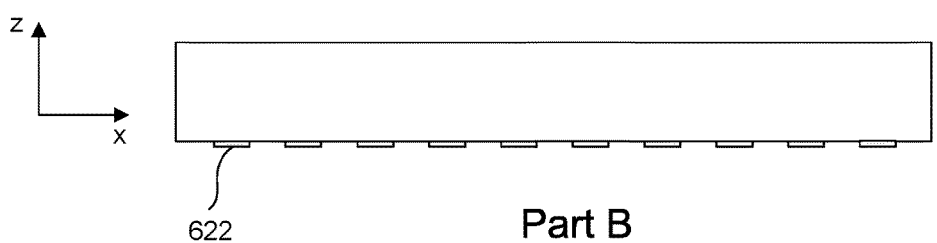

FIG. 6 depicts different schematic views of a chip 620. In some embodiments, the chip may be a display driver chip. The chip may be a high performance readout integrated circuit (ROIC) chip that has been configured for adapted for neural recording. In some embodiments, the chip may be a m×n pixel read out integrated circuit (ROIC) imaging chip with a total of m×n pixels/electrodes over an array area. The array area may be given by X1×Y1. In some embodiments, X1=Y1 such that the array has a square shape. In other embodiments, X1≠Y1 such that the array has a rectangular shape. The chip can be configured to acquire data at a rate of millions of pixels per second. The chip may have an adjustable gain current amplifier in each pixel circuit can be controlled by a series of input and output boards through a computer. The chip may be a multiplexed current readout chip with a gain amplifier in each unit cell or pixel.

The chip may include an m×n two-dimensional array of bond pads 622 corresponding to the pixel array. Each of the bond pads may be individually addressable and configured to drive a pixel on a separate display (e.g., an LED or LCD-based display, not shown). The bond pads may be spaced apart by a pitch $p_x$ along an x-axis and by a pitch $p_y$ along a y-axis. The pitches $p_x$ and $p_y$ may be constant or variable. The pitches $p_x$ and $p_y$ may be the same or different. In some embodiments, each of the pitches $p_x$ and $p_y$ may be 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, or greater than 20 μm. The pitch of the bond pads on the chip may be customized based on the pitch of the substrate wire bumps. Conversely, the pitch of the substrate wire bumps may be customized based on the pitch of the bond pads on the chip.

In some embodiments, the plurality of pixels and the plurality of bonding pads may be provided in different array configurations. For example, in some instances (not shown), the plurality of pixels may be provided in a rectangular array, and the plurality of bonding pads may be provided in a non-rectangular array (e.g., a hexagonal array).

The bond pads may be formed of a regular shape or irregular shape, and may be formed having the same size or different sizes. Examples of regular shapes include rectangular, square, triangular, circular, elliptical, hexagonal, or any other known regular shapes. In some embodiments, the bond pads may include a mixed array of bond pads comprising bond pads of different shapes and/or sizes. The bond pads may be arranged in a regular pattern array. Alternatively, the bond pads may be arranged in an irregular pattern. The sizes of the bond pads may be determined by their dimensions, for example by their lengths, widths, heights, diameters, thicknesses, etc., depending on the shape and structural configuration in which the bond pads are formed. In some embodiments, all the bond pads may have the same height. In other embodiments, the bond pads may be formed having different heights. The bond pads may also have the same lateral dimensions (e.g., same diameter or length/width). Alternatively, the bond pads may have different lateral dimensions (e.g. different diameters or different lengths/widths). In some embodiments, the bond pads may be formed having a curved surface profile. The curved surface profile may be convex (e.g. semispherical bond pad) or concave (e.g. a concaved dimple formed on the surface of the bond pad). The layout of the bond pads may or may not directly match the geometry of the distal portion of the plurality of wires. For example, a hexagonal pixel array may closely match a plurality of wires that are arranged in a hexagonal closed-packed configuration. In contrast, a rectangular pixel array may match the plurality of wires (arranged in a hexagonal closed-packed configuration) to a lesser degree compared to the hexagonal pixel array.

The proximal portion of one or more wires may be connected to a bond pad. Alternatively, the proximal portion of each wire may be connected to each bond pad. In some embodiments, the pitch of the substrate wire bumps and the pitch of the bond pads on the chip may be configured such that the substrate wire bumps and the bond pads have a 1:1 correspondence. In other embodiments, the pitch of the substrate wire bumps and the pitch of the bond pads on the chip may be configured such that the substrate wire bumps and the bond pads have a n:1 correspondence, where n is an integer greater than 1. For example, in those other embodiments, the substrate wire bumps and the bond pads can have a 2:1, 3:1, 4:1, 5:1, 6:1, 7:1, 8:1, 9:1, 10:1, or a greater than 10:1 correspondence.

In some embodiments, the plurality of bond pads may occupy a significant fraction of the total surface area on the pixel region of the pixel side of the chip. For example, the bond pads may occupy 50%, 60%, 70%, 80%, or more than 80% of the total surface area on the pixel side of the chip. In some cases, a diameter of a substrate wire bump (or wire pad) may be substantially less than or equal to a size of the gap between adjacent bond pads on the chip. The per-wire connectivity may be a function of the percentage of space occupied by bond pads. The probability of two pixels connecting to a same wire may be reduced when the diameter of a substrate wire bump (or wire pad) is substantially less than the size of the gap between adjacent bond pads.

In some other embodiments, the diameter and/or surface area of a substrate wire bump (or wire pad) may be large relative to an outer diameter of the wire. This may be due to the wire having a thin wire insulating layer, and/or over-etching of the insulating layer to expose the substrate wire bump (or wire pad). In these embodiments, the probability of two pixels connecting to a same wire may be higher. In order to reduce such probability, the size of the gap between adjacent bond pads may be increased.

In some alternative embodiments, the pitch of the substrate wire bumps and the pitch of the bond pads on the chip may be configured such that the substrate wire bumps and the bond pads have a 1:n correspondence, where n is an integer greater than 1.

In some embodiments, one or more pixels on the chip may be used as ground electrodes. Accordingly, those one or more pixels may be grounded, instead of being active pixels. One or more wires may be connected to those "ground" pixels. Those wires may or may not include an insulating layer.

To form a neural-interface probe in accordance with the present invention, the chip needs to be mechanically and electrically coupled to the wire bundle substrate (or vice versa). As previously described in FIG. 1, the mechanical/electrical coupling may be provided by a plurality of interconnects 130 formed at an interface between the chip and the wire bundle substrate. The proximal portion of the plurality of wires may be connected to the plurality of bond pads via the plurality of interconnects formed between the chip and the substrate. The interconnects allow the electrodes at the distal portion of the wires to be in electrical communication with the integrated circuit elements on the chip, during monitoring and/or stimulation of brain activity. Various interconnect structures and assembly methods thereof in association with the fabrication of a neural-interface probe are next described with reference to FIGS. 7 through 17.

Figure 7:
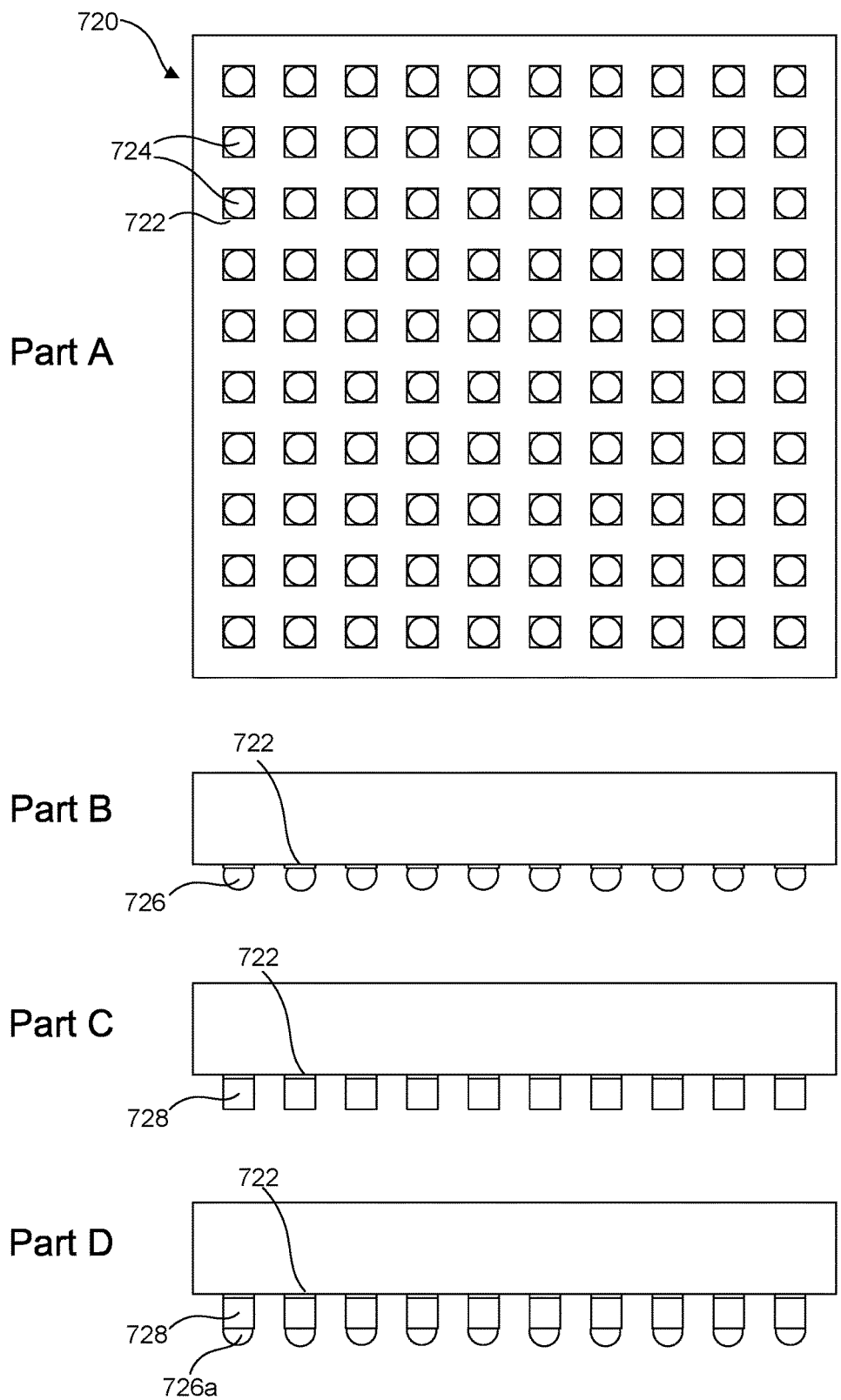
FIG. 7 Parts A, B, C, and D show examples of protrusions being formed on bonding pads of a chip, in accordance with some embodiments.

In some embodiments, protrusions may be formed on the bond pads of a chip to increase a stand-off height between the chip and a wire bundle substrate. The increased stand-off height can aid in interconnect formation, for example by increasing surface area wettability (when using solder interconnects). Referring to FIG. 7, a chip 720 may comprise a plurality of bond pads 722. A plurality of protrusions 724 may be formed on the plurality of bond pads 722. The protrusions may comprise solder bumps 726 (part B), conductive pillars 728 (part C), and/or conductive pillars 728 with solder caps 726a (part D). The solder bumps may be formed of any type of binary or ternary solder alloys. In some cases, the solder bumps and/or solder caps may be formed of a lead-free solder such as SnAg, or a SnAg alloy (e.g., SnAgCu). In some instances, the solder bumps and/or solder caps may be formed of a low melting point metal or metallic alloy (e.g., In, or an In alloy). The solder bumps may have low levels of toxicity, and may not contain toxic metals such as Pb. The solder bumps can be screen printed, electroplated, or solder jetted. In some cases, solder balls may be physically placed onto the bond pads of the chip and reflowed to form the solder bumps. The conductive pillars may be formed of a metal (e.g., Cu, Au, Ag, Pt, Pd, etc.). Alternatively, the conductive pillars may be formed of a conductive polymer. The conductive pillars may be electroplated (e.g., when the conductive pillar is a metal) or dispensed (e.g., when the conductive pillar is formed of a liquid conductive polymer). The solder caps are usually used in conjunction with a metal pillar, and can be formed by electroplating solder on the top exposed surface of the metal pillar. Electrical contact for the electroplating process can be established via a seed layer and/or sacrificial layer. In addition to electroplating, other deposition techniques such as electroless deposition, sputtering, evaporation, e-beam evaporation, chemical vapor deposition, and the like can be used to form the protrusions.

Figure 8:
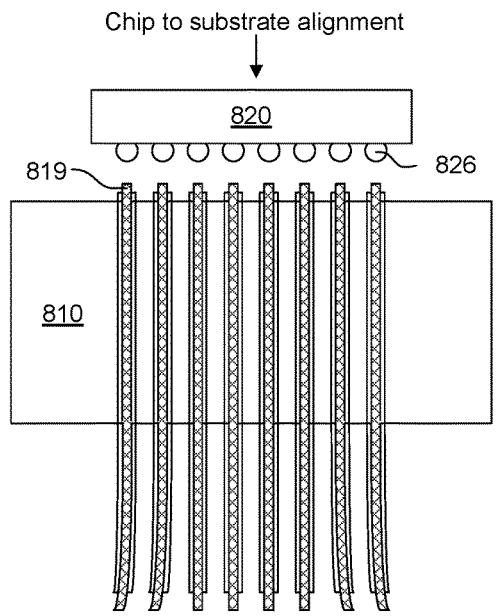
FIG. 8 Parts A, B, C, and D show an example of a neural-interface probe and methods of forming thereof, in accordance with various embodiments.
Figure 8:
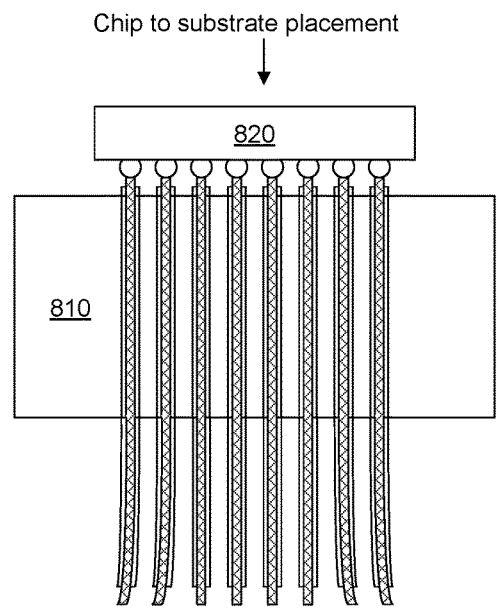
Figure 8:
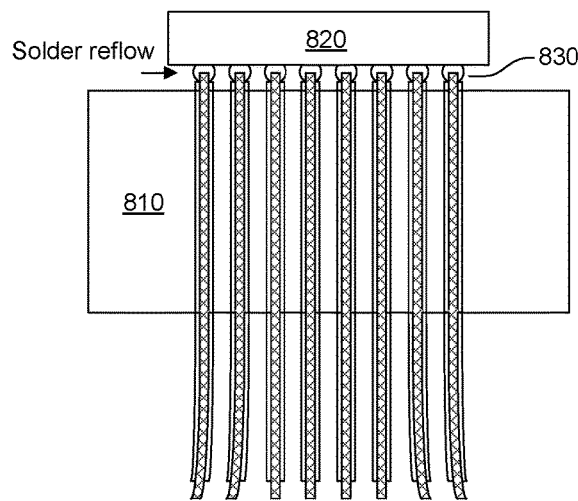
Figure 8:
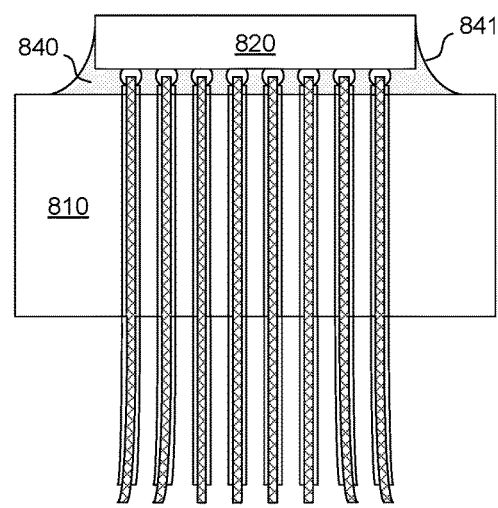

FIG. 8 illustrates a neural-interface probe and a method of forming the probe in accordance with some embodiments. Referring to part A, a chip 820 may comprise a plurality of solder bumps 826 formed on the bond pads (not shown) of the chip. The proximal portion of the wires on a wire bundle substrate 810 may comprise a plurality of substrate wire bumps 819. The chip and the wire bundle substrate may be aligned, by aligning the solder bumps on the chip to the substrate wire bumps on the substrate (part A). In some cases, the chip and the wire bundle substrate may be aligned to a precision within 10 μm. After the solder bumps have been aligned to the substrate wire bumps, the chip is placed onto the wire bundle substrate (part B). Next, the assembly of part B undergoes a reflow process during which the solder bumps melt and wet the substrate wire bumps to form a plurality of interconnects 830 (part C). During the reflow process, heat may be provided to melt the solder bumps. For example, the assembly of part B may be placed in an oven (e.g., a conveyor belt convection oven or a stand-alone convection oven) capable of achieving temperatures to reflow the solder. Next, an epoxy resin is dispensed into the gap between the chip and wire bundle substrate to form an underfill 840 to protect the interconnects (part D). The epoxy resin (underfill) may be biocompatible. The underfill can also help to relieve thermomechanical stresses in the assembly of part D, by compensating for any mismatch in the coefficients of thermal expansion (CTEs) between the chip and the substrate. In some cases, the epoxy resin may be dispensed on the substrate near an edge of the chip, and the epoxy resin may flow through the gap between the chip and the substrate via capillary action. In some cases, the speed of the capillary action (flow of epoxy resin through the gap) can be increased with aid of a vacuum or negative pressure. The epoxy resin may be cured (hardened) to form the underfill 840. The curing process may include applying heat to the epoxy resin, for example by placing the assembly of part D into a convection oven. Proper dispense and curing of the underfill can result in a smooth fillet 841 between the edges of the chip and the surface of the substrate. The fillet 841 can help to mitigate thermomechanical stresses induced in the probe during the above assembly steps (e.g., during the solder reflow and/or underfill curing steps).

In some embodiments, a solder flux may be dispensed on the solder bumps of the chip prior to the assembly process. The solder flux can remove oxides from the surface of the solder bumps, thereby improving the wetting behavior of the solder during reflow. In some cases, the solder flux may leave behind flux residues after the reflow process. The flux residues may affect the interfacial adhesion between the underfill and various contact surfaces on the chip/substrate. To improve package reliability, the flux residues may be removed or minimized. The flux residues can be removed using a deflux process prior to the underfilling step in part D. The deflux process may include using water (for water soluble fluxes) and/or other types of suitable solvents to remove the flux residues. In some cases, a solder flux may be omitted, and the solder reflow step in part C may be performed in a reducing environment (e.g., comprising $H_2$ gas) to remove oxides from the solder bumps.

Figure 9:
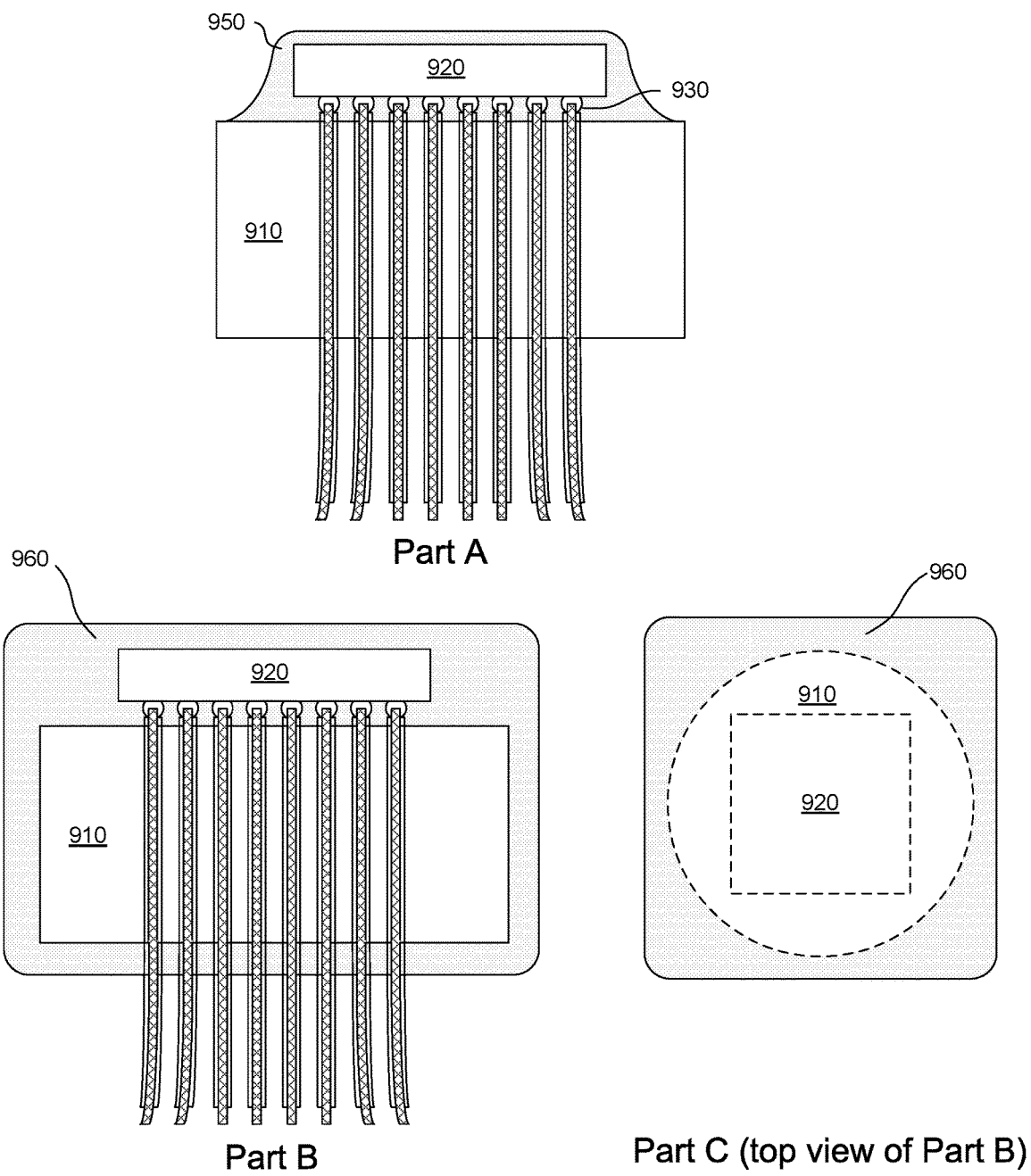
FIG. 9 Parts A, B, and C show an example of a neural-interface probe and methods of forming thereof, in accordance with various embodiments.

FIG. 9 illustrates the use of additional packaging materials to reinforce the neural-interface probe shown in part D of FIG. 8. Referring to part A of FIG. 9, an encapsulating material may be dispensed on the surrounding areas on the chip and the wire bundle substrate to form an encapsulation layer 950. The encapsulation layer may serve to further protect the regions surrounding the chip. In some cases, an underfill may be omitted and the encapsulating material may be dispensed into the gap between the chip and wire bundle substrate (i.e., the encapsulating material may also serve as an underfill). In some further embodiments, the assembly in part A of FIG. 9 may undergo an overmolding process to form a housing 960 sealing the chip and the substrate, while leaving the distal portion of the wires freely extending. Parts B and C of FIG. 9 respectively show a cross-sectional side view and a top view of the probe with the housing. The materials used in the encapsulation layer and the housing may be biocompatible. In some cases, the housing may be configured to hermetically seal the chip and the substrate. In some embodiments, the housing may be configured to provide structural rigidity to the probe along a longitudinal direction that is substantially parallel to the plurality of wires.

Figure 10:
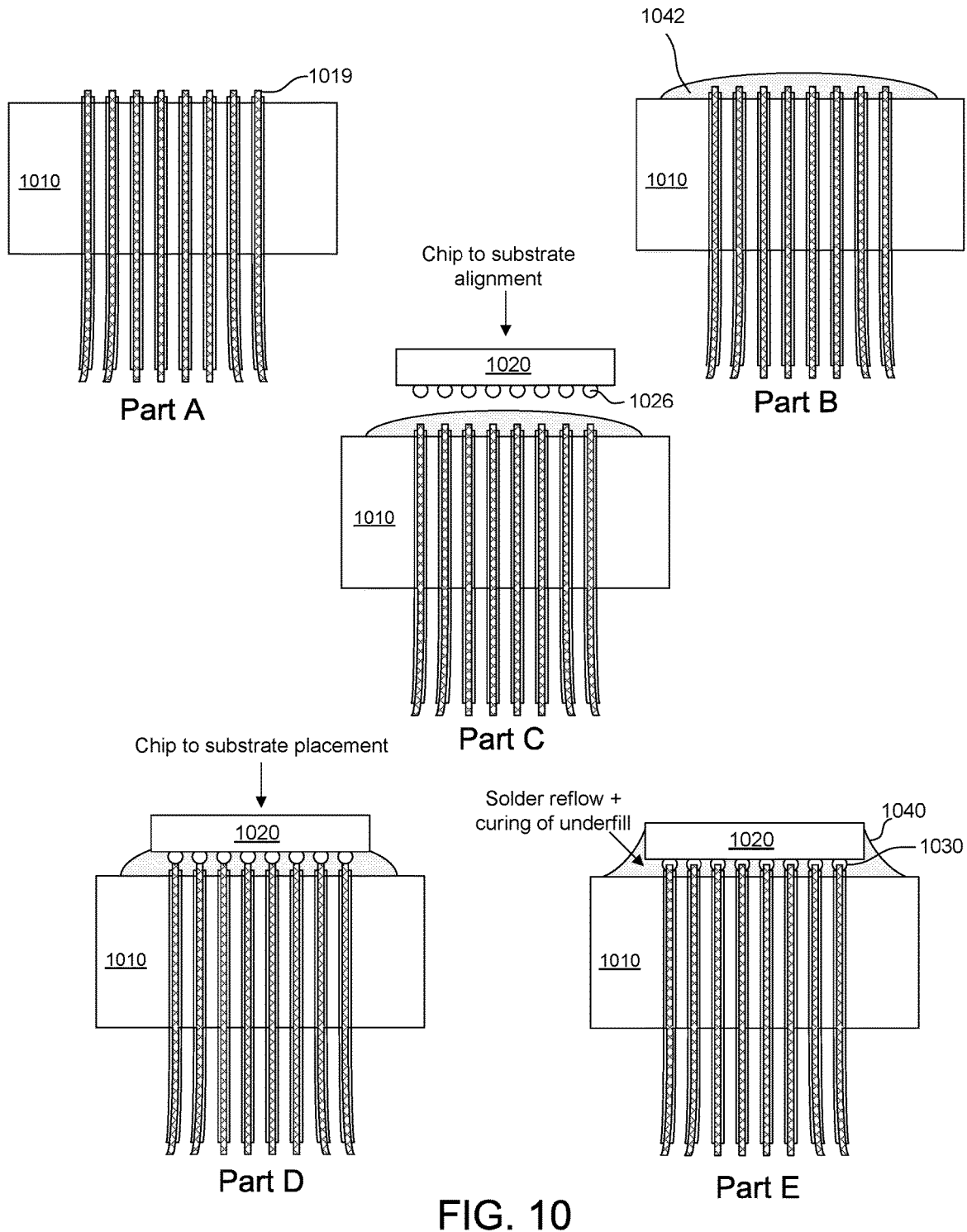
FIG. 10 Parts A, B, C, D, and E show an example of a neural-interface probe and methods of forming thereof, in accordance with various embodiments.

FIG. 10 illustrates a neural-interface probe and a method of forming the probe in accordance with some embodiments. The embodiment of FIG. 10 may be similar to the embodiment of FIG. 8 except for the following differences. In FIG. 10, an epoxy resin (underfill) is first dispensed onto the wire bundle substrate prior to formation of the interconnects. In contrast, in FIG. 8, the epoxy resin is dispensed onto the wire bundle substrate after the interconnects have been formed.

Referring to part A of FIG. 10, the proximal portion of the wires on a wire bundle substrate 1010 may comprise a plurality of substrate wire bumps 1019. A no-flow underfill 1042 may be dispensed onto the wire bundle substrate prior to connecting the chip to the substrate (part B). The no-flow underfill may be an epoxy resin comprising a solder flux component. The solder flux component may be a no-clean flux that generates a low amount of flux residue, and/or that leaves behind flux residue that is chemically compatible with the other packaging materials used in the probe. The epoxy resin and the solder flux component (and residues) may be biocompatible. As previously described, the solder flux component can remove oxides from the surface of the solder bumps, thereby improving the wetting behavior of the solder during the reflow process. A chip 1020 comprising a plurality of solder bumps 1026 may be provided. The chip and the wire bundle substrate may be aligned, by aligning the solder bumps on the chip to the substrate wire bumps (part C). After the solder bumps have been aligned to the substrate wire bumps, the chip is placed onto the wire bundle substrate (part D). Next, the assembly of part D is subjected to a reflow process during which (1) the solder bumps melt and wet the substrate wire bumps to form a plurality of interconnects 1030, and (2) the no-flow underfill cures (hardens) to form underfill 1040 protecting the interconnects (part E). Accordingly, the interconnect formation and underfill curing can be performed in a single reflow step in the embodiment of FIG. 10.

Figure 11:
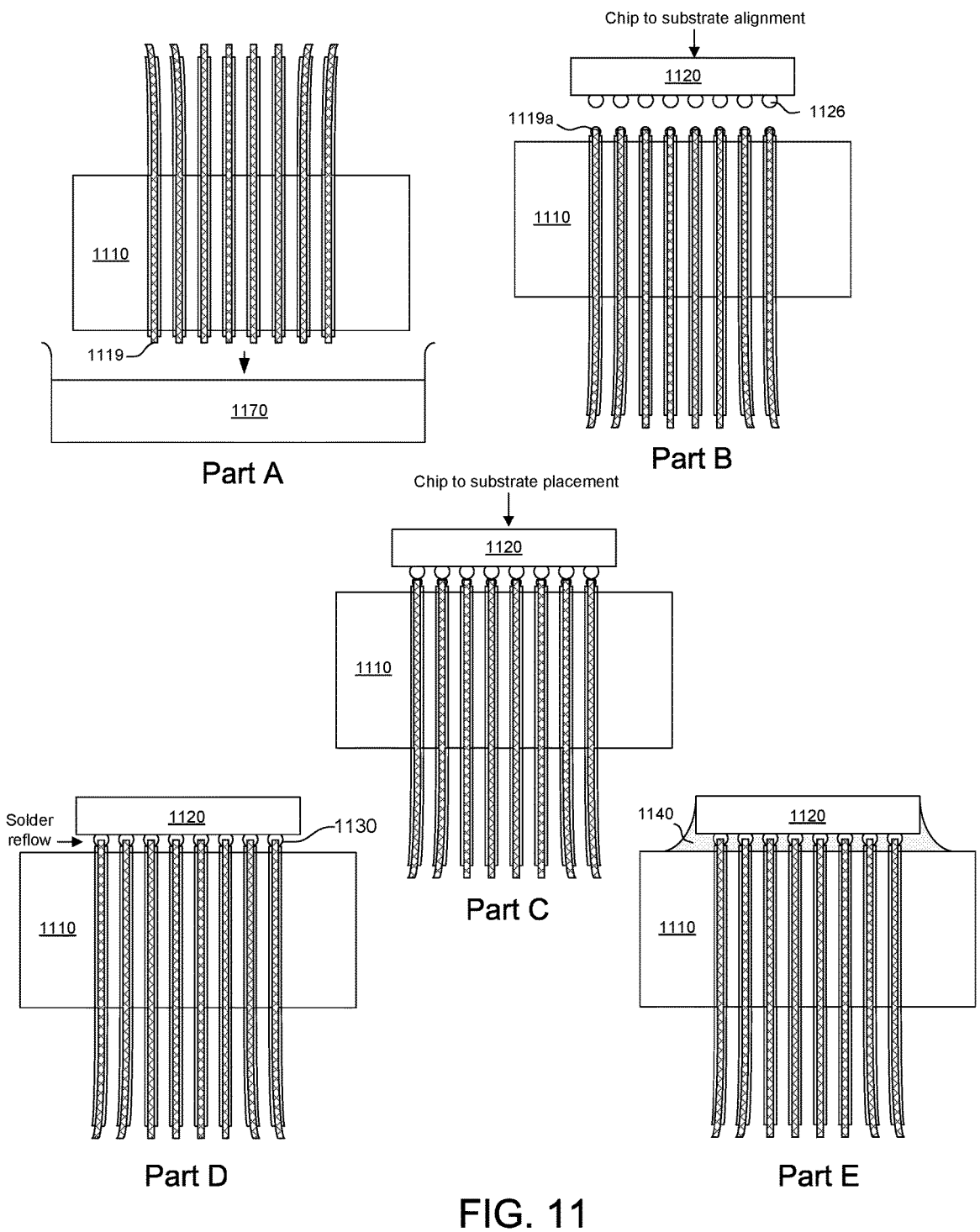
FIG. 11 Parts A, B, C, D, and E show an example of a neural-interface probe and methods of forming thereof, in accordance with various embodiments.

FIG. 11 illustrates a neural-interface probe and a method of forming the probe in accordance with some embodiments. In FIG. 11, solder caps 1119a may be formed on substrate wire bumps 1119 to improve solder wettability and self-alignment between a chip 1120 and a wire bundle substrate 1110. Referring to part A, the proximal portion of the wire bundle substrate (comprising the substrate wire bumps 1119) may be dipped into a solder bath 1170. The solder bath may contain any type of binary or ternary solder alloys. In some cases, the solder bath may contain a lead-free solder such as SnAg, or a SnAg alloy (e.g., SnAgCu). In some instances, the solder bath may contain a low melting point metal (e.g., In, or an In alloy). The solder bath may have low levels of toxicity, and may not contain toxic metals such as Pb. The solder bath may be in a molten state. The solder may wet the substrate wire bumps to form solder caps 1119a on the substrate wire bumps, upon removing the substrate from the solder bath. The solder caps may form conformally as a thin layer on the surface of the substrate wire bumps. In some cases, the solder caps may have a semi-hemispherical shape at a tip of the substrate wire bumps. Next, the chip and the wire bundle substrate may be aligned, by aligning the solder bumps on the chip to the solder-capped substrate wire bumps on the substrate (part B). After the alignment is completed, the chip is placed onto the wire bundle substrate (part C). Next, the assembly of part C undergoes a reflow process during which the solder bumps (on the chip) and the solder caps (on the substrate wire bumps) melt and join together to form a plurality of interconnects 1130 (part D). Next, an epoxy resin is dispensed into the gap between the chip and wire bundle substrate to form an underfill 1140 to protect the interconnects (part E). The underfill can also help to relieve the thermomechanical stresses in the assembly of part E, by compensating for any mismatch in the coefficients of thermal expansion (CTEs) between the chip and the substrate. In some embodiments, a solder flux may be dispensed on the solder bumps and solder caps prior to the interconnect formation. The solder flux can remove oxides from the surfaces of the solder bumps and solder caps, thereby improving the wetting behavior of the solder during the reflow process.

Figure 12:
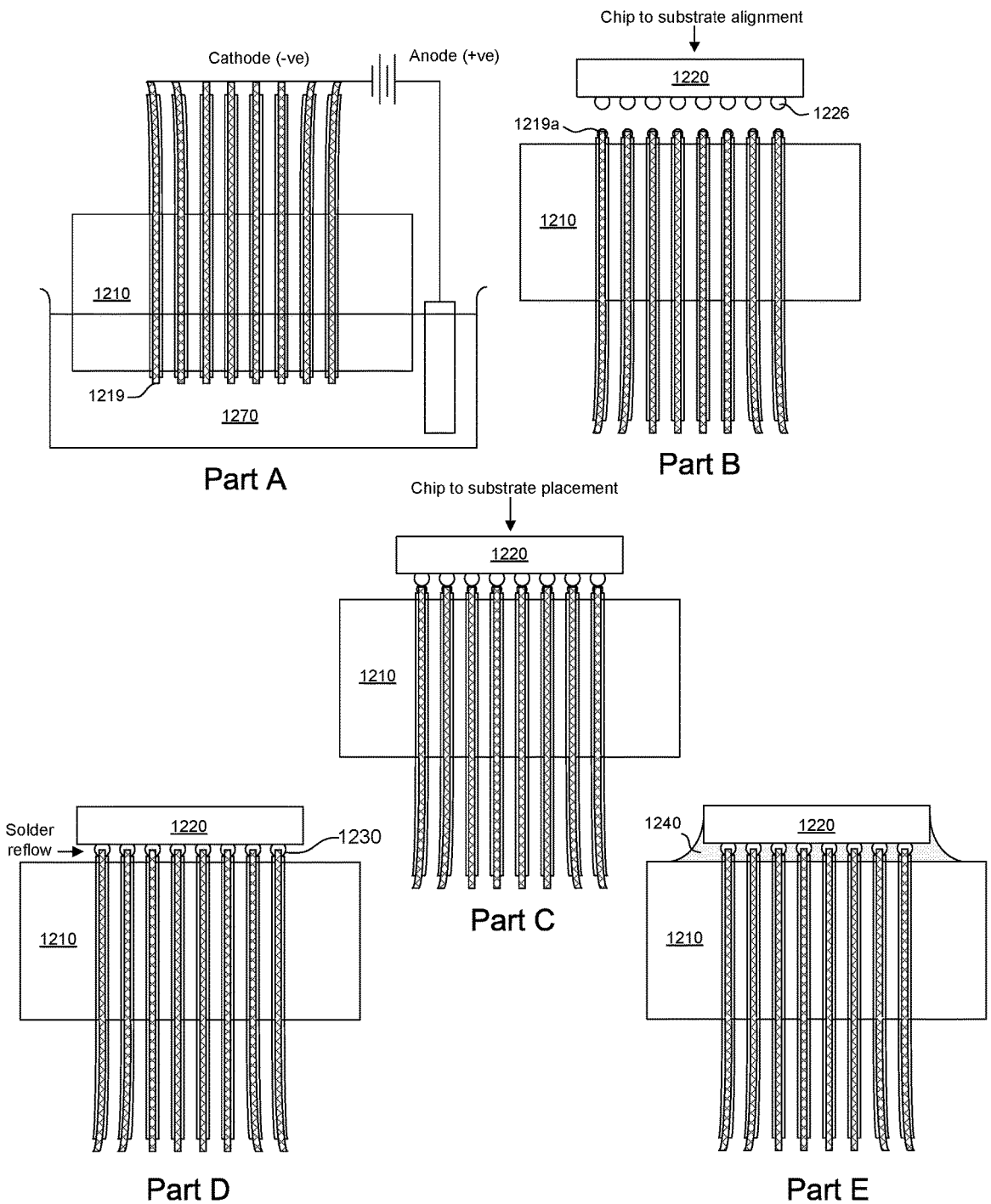
FIG. 12 Parts A, B, C, D, and E show an example of a neural-interface probe and methods of forming thereof, in accordance with various embodiments.

FIG. 12 illustrates a neural-interface probe and a method of forming the probe in accordance with some embodiments. The embodiment of FIG. 12 may be similar to the embodiment of FIG. 11, except solder caps 1219a in FIG. 12 are formed by electroplating solder onto the substrate wire bumps 1219. The electroplating process may be performed by immersing the substrate wire bumps into an electroplating bath 1270 (part A). The remaining assembly steps in parts B, C, D, and E of FIG. 12 may be similar to those previously described in FIG. 11.

Figure 13:
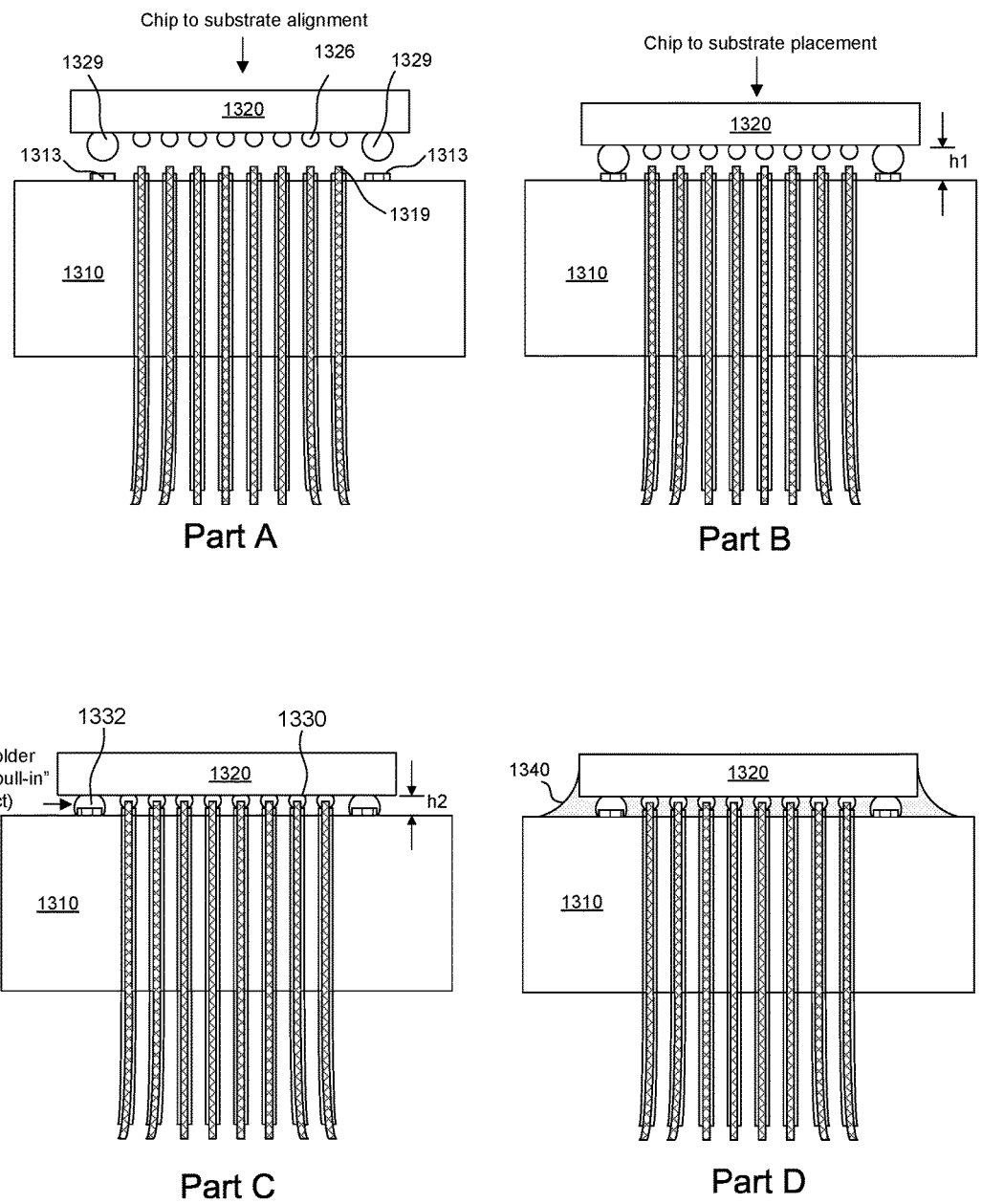
FIG. 13 Parts A, B, C, and D show an example of a neural-interface probe and methods of forming thereof, in accordance with various embodiments.

FIG. 13 illustrates a neural-interface probe and a method of forming the probe in accordance with some embodiments. The embodiment of FIG. 13 may be similar to the embodiment of FIG. 8 except for the following differences. In FIG. 13, a chip 1320 may comprise solder bumps of different sizes. For example, the chip may comprise a first set of solder bumps 1326 and a second set of solder bumps 1329. The first set of solder bumps may be used to form electrical interconnects 1330 with a plurality of substrate wire bumps 1319 on a wire bundle substrate 1310. The second set of solder bumps may be used to form interconnects 1332 with a plurality of alignment pads 1313 on the wire bundle substrate. The second set of solder bumps may be used to enhance the solder self-alignment of the chip to the substrate. For example, the second set of solder bumps may be used for coarse alignment of the chip to the substrate, followed by fine alignment of the chip to the substrate using the first set of solder bumps.

The interconnects 1332 formed by the second set of solder bumps and the alignment pads may or may not be connected to integrated circuits on the chip 1320. In some cases, the interconnects 1332 formed by the second set of solder bumps and the alignment pads may be purely mechanical structures. In other cases, the interconnects 1332 formed by the second set of solder bumps and the alignment pads may be used to carry electrical signals and/or power between the chip and an external device, as described later with reference to FIG. 17. The external device may be, for example a computer or a power source.

The first and second sets of solder bumps may have different sizes. For example, as shown in part A, the second set of solder bumps may be larger than the first set of solder bumps. In some cases, the second set of solder bumps may be 10%, 20%, 30%, 40%, 50%, 60%, 70%, 80%, 90%, 100%, 150%, or 200% larger than the first set of solder bumps. The first and second sets of solder bumps may be located on different portions of the chip. For example, the first set of solder bumps may be located at a central portion of the chip, and the second set of solder bumps may be located at a peripheral portion of the chip. The second set of solder bumps may be disposed surrounding the first set of solder bumps. In some cases, the second set of solder bumps may be located along opposing edges of the chip. In other cases, the second set of solder bumps may be located only at the corners of the chip. Alternatively, in some other cases, the second set of solder bumps may be interspersed uniformly among the first set of solder bumps over an entire surface of the chip. Any placement of the second set of solder bumps relative to the first set of solder bumps may be contemplated. The first and second sets of solder bumps may be formed of a same solder material. The solder material may comprise lead-free solder such as SnAg, or a SnAg alloy (e.g., SnAgCu). In some instances, the solder material may comprise a low melting point metal (e.g., In, or an In alloy). Alternatively, the first and second sets of solder bumps may be formed of different solder materials having different material properties (e.g., melting point, yield strength, etc.). In some embodiments, the second set of solder bumps may have a lower melting point than the first set of solder bumps. For example, the melting point of the second set of solder bumps may be 5%, 10%, 15%, 20%, 25%, 30%, 35%, 40%, 45%, or 50% lower than the melting point of the first set of solder bumps. Alternatively, in some other embodiments, the second set of solder bumps may have a higher melting point than the first set of solder bumps. The first and second sets of solder bumps may have low levels of toxicity, and may not contain toxic metals such as Pb.

Referring to part A of FIG. 13, the chip and the wire bundle substrate may be aligned. For example, the second set of solder bumps 1329 may be aligned to the alignment pads 1313. Since the size of the second set of solder bumps/alignment pads is greater than the size of the first set of solder bumps/substrate wire bumps, the need for highly precise alignment can be reduced, which can improve assembly throughput time.

After the second set of solder bumps have been aligned to the alignment pads, the chip is placed onto the wire bundle substrate (part B). Since the second set of solder bumps may be larger than the first set of solder bumps, the size of the second set of solder bumps may substantially dictate an initial stand-off height (gap) h1 between the chip and the substrate.

Next, the assembly of part B undergoes a reflow process during which the solder bumps 1326 and 1329 melt and wet the substrate wire bumps 1319 and alignment pads 1313 to form a plurality of interconnects 1330 and 1332 (part C). The reflow process may be a dual solder reflow process in which the first and second sets of solder bumps may be simultaneously or sequentially melted. For example, when the second set of solder bumps have a lower melting point than the first set of solder bumps, the second set of solder bumps may first melt at a first temperature T1 and the second set of solder bumps may melt at a second temperature T2 during the reflow process, whereby T2>T1. The difference between the first and second temperatures may be given by $\Delta T = T2 - T1$. In some cases, $\Delta T$ may be 2°, 4°, 6°, 8°, 10°, 12°, 14°, 16°, 18°, 20°, or more than 20°. At the first temperature T1, the second set of solder bumps may "pull-in" the chip to the substrate in a coarse alignment step, to compensate for any relative movement/misalignment between the chip and the substrate during the placement step and/or reflow process. At the second temperature T2, the first set of solder bumps may melt and wet the substrate wire bumps in a fine alignment step. The coarse alignment and fine alignment steps can correct for rotational and/or translational displacements between the chip and the substrate. As shown in part C, the chip and the substrate may have a stand-off height h2 after the interconnects have been formed, whereby h2<h1 due to the solder "pull-in" effect.

Next, an epoxy resin is dispensed into the gap between the chip and wire bundle substrate to form an underfill 1340 to protect the interconnects (part D). The underfill can also help to relieve the thermomechanical stresses in the assembly of part D, by compensating for any mismatch in the coefficients of thermal expansion (CTEs) between the chip and the substrate.

Figure 14:
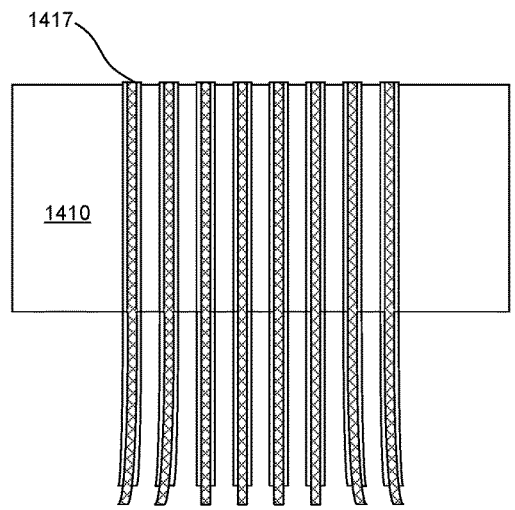
FIG. 14 Parts A, B, C, and D show an example of a neural-interface probe and methods of forming thereof, in accordance with various embodiments.
Figure 14:
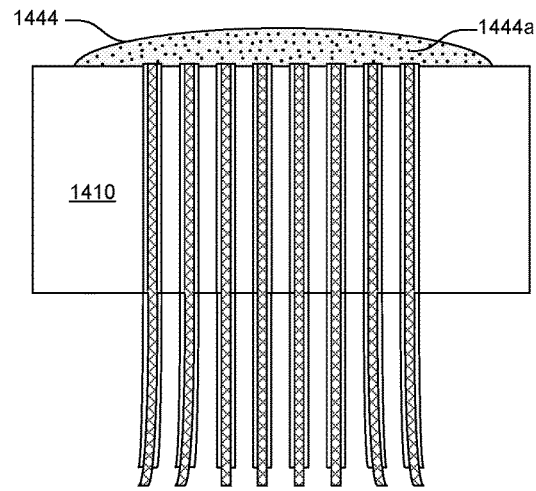
Figure 14:
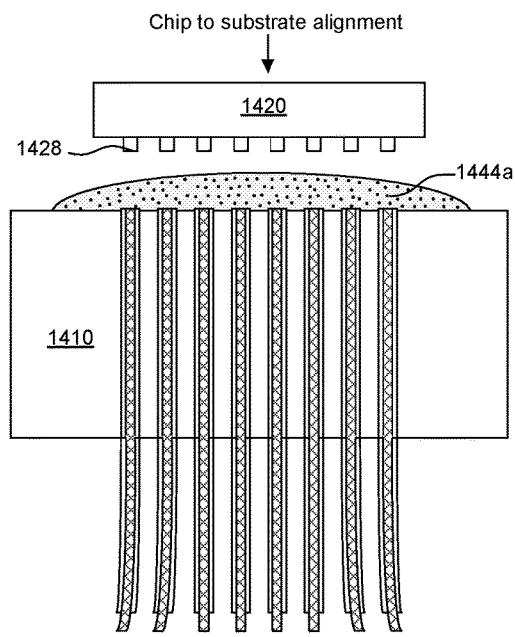
Figure 14:
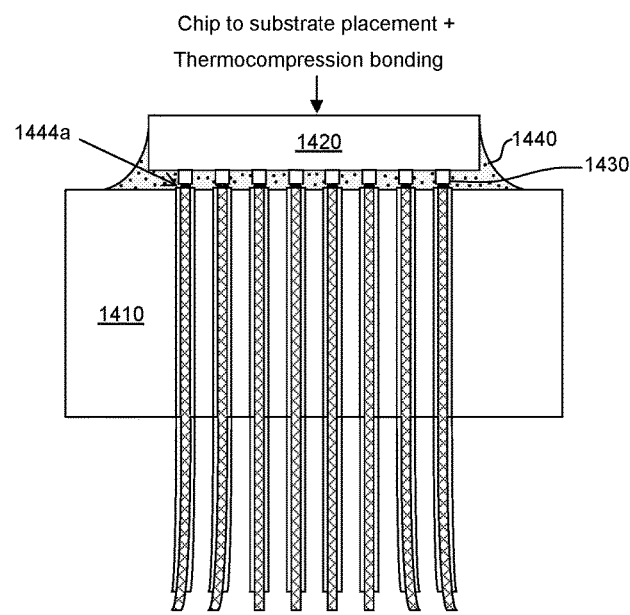

FIG. 14 illustrates a neural-interface probe and a method of forming the probe in accordance with some embodiments. The embodiment in FIG. 14 may be different from the embodiments in FIGS. 8 through 13, in that the interconnects in FIG. 14 do not include solder.

Referring to part A of FIG. 14, the proximal portion of the wires on a wire bundle substrate 1410 may comprise a plurality of connection pads 1417. The connection pads 1417 may be similar to the connection pads 317 previously described in FIG. 3. Next, an anistropic conductive adhesive (ACA) 1444 may be dispensed onto the wire bundle substrate over the connection pads (part B). The anistropic conductive adhesive may comprise an epoxy resin containing a plurality of conductive particles 1444a. The anistropic conductive adhesive may be biocompatible. The conductive particles can provide electrical connection in a z-direction, and can be used to form interconnects. The epoxy resin may serve as an underfill after curing. The conductive particles may be distributed spaced apart in the x-y direction such that they do not cause shorting between adjacent interconnects. In some embodiments, an anistropic conductive film (ACF) may be used instead of an ACA. The ACF has similar properties to the ACA, except the ACF is laminated on the wire bundle substrate over the connection pads (instead of being dispensed in liquid form).

Referring to part C, a chip 1420 comprising a plurality of conductive pillars 1428 may be provided. The conductive pillars 1428 may be similar to the conductive pillars 728 shown in part C of FIG. 7. The chip and the wire bundle substrate may be aligned, by aligning the conductive pillars on the chip to the connection pads on the substrate (part C). After the conductive pillars have been aligned to the connection pads, the chip is placed onto the wire bundle substrate and bonded to the substrate via a thermocompression bonding process (part D). During the thermocompression bonding process, heat and pressure is applied such that the conductive pillars are pressed onto the connection pads with conductive particles 1444a trapped between the interfaces, thereby forming a plurality of interconnects 1430. During the thermocompression bonding process, the epoxy resin in the anistropic conductive adhesive (or anistropic conductive film) cures to form underfill 1440 protecting the interconnects (part D). Accordingly, the interconnect formation and underfill curing can be performed via a single thermocompression bonding step in the embodiment of FIG. 14.

Figure 15:
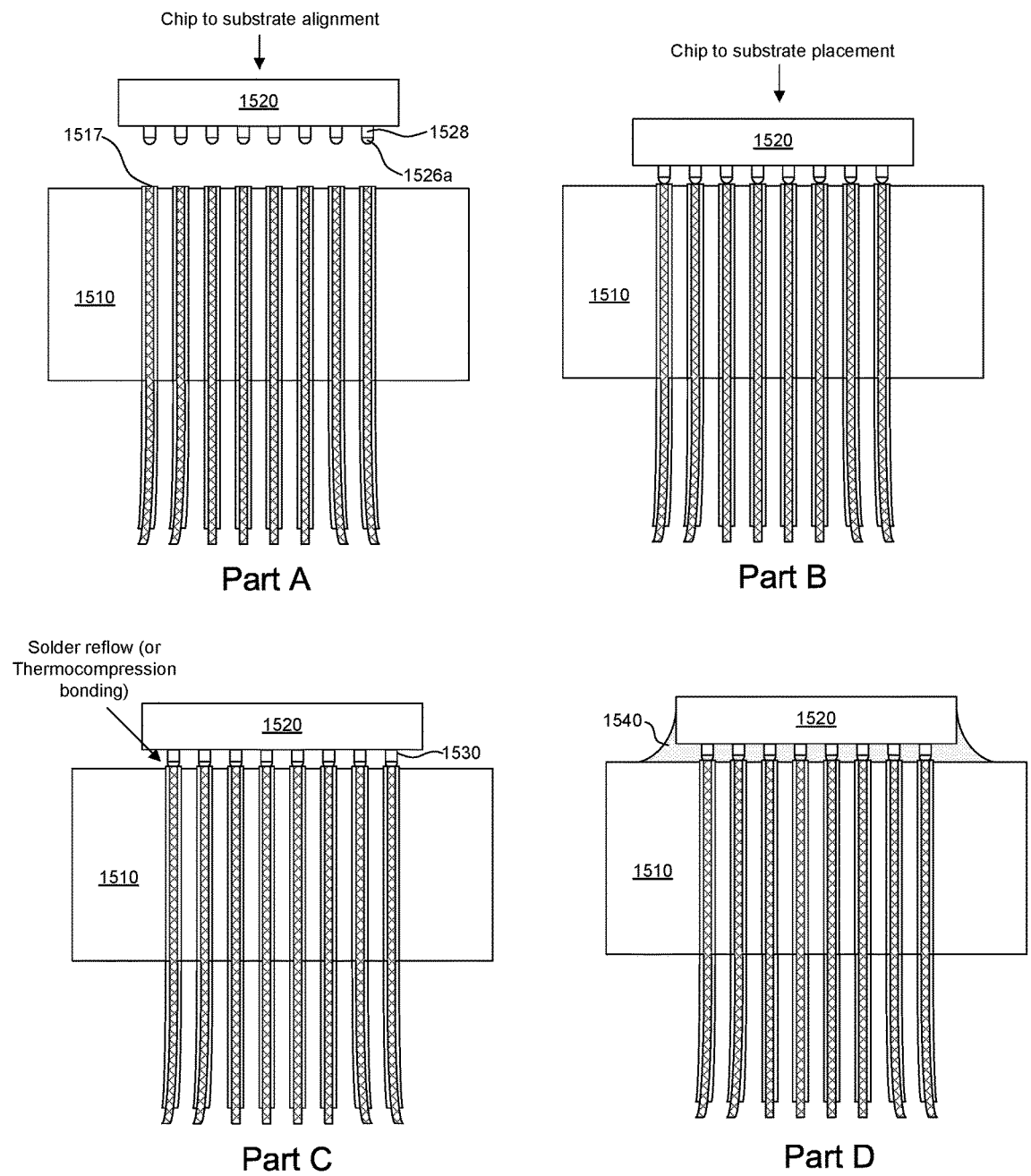
FIG. 15 Parts A, B, C, and D show an example of a neural-interface probe and methods of forming thereof, in accordance with various embodiments.

FIG. 15 illustrates a neural-interface probe and a method of forming the probe in accordance with some embodiments. Referring to part A of FIG. 15, the proximal portion of the wires on a wire bundle substrate 1510 may comprise a plurality of connection pads 1517. The connection pads 1517 may be similar to the connection pads 1417 previously described in FIG. 14. A chip 1520 comprising a plurality of conductive pillars 1528 with solder caps 1526a may be provided, similar to that shown in part D of FIG. 7. The chip and the wire bundle substrate may be aligned, by aligning the solder-capped conductive pillars to the connection pads on the substrate (part A). After the solder-capped conductive pillars have been aligned to the connection pads, the chip is placed onto the wire bundle substrate (part B). Next, the assembly of part B undergoes a reflow process during which the solder caps (on the conductive pillars) melt and wet the connection pads on the substrate to form a plurality of interconnects 1530 (part C). In some cases, the chip may be bonded to the substrate using a thermocompression process by applying heat and pressure, instead of using a reflow process. Next, an epoxy resin is dispensed into the gap between the chip and wire bundle substrate to form an underfill 1540 to protect the interconnects (part D). The underfill can also help to relieve the thermomechanical stresses in the assembly of part D, by compensating for any mismatch in the coefficients of thermal expansion (CTEs) between the chip and the substrate.

Figure 16:
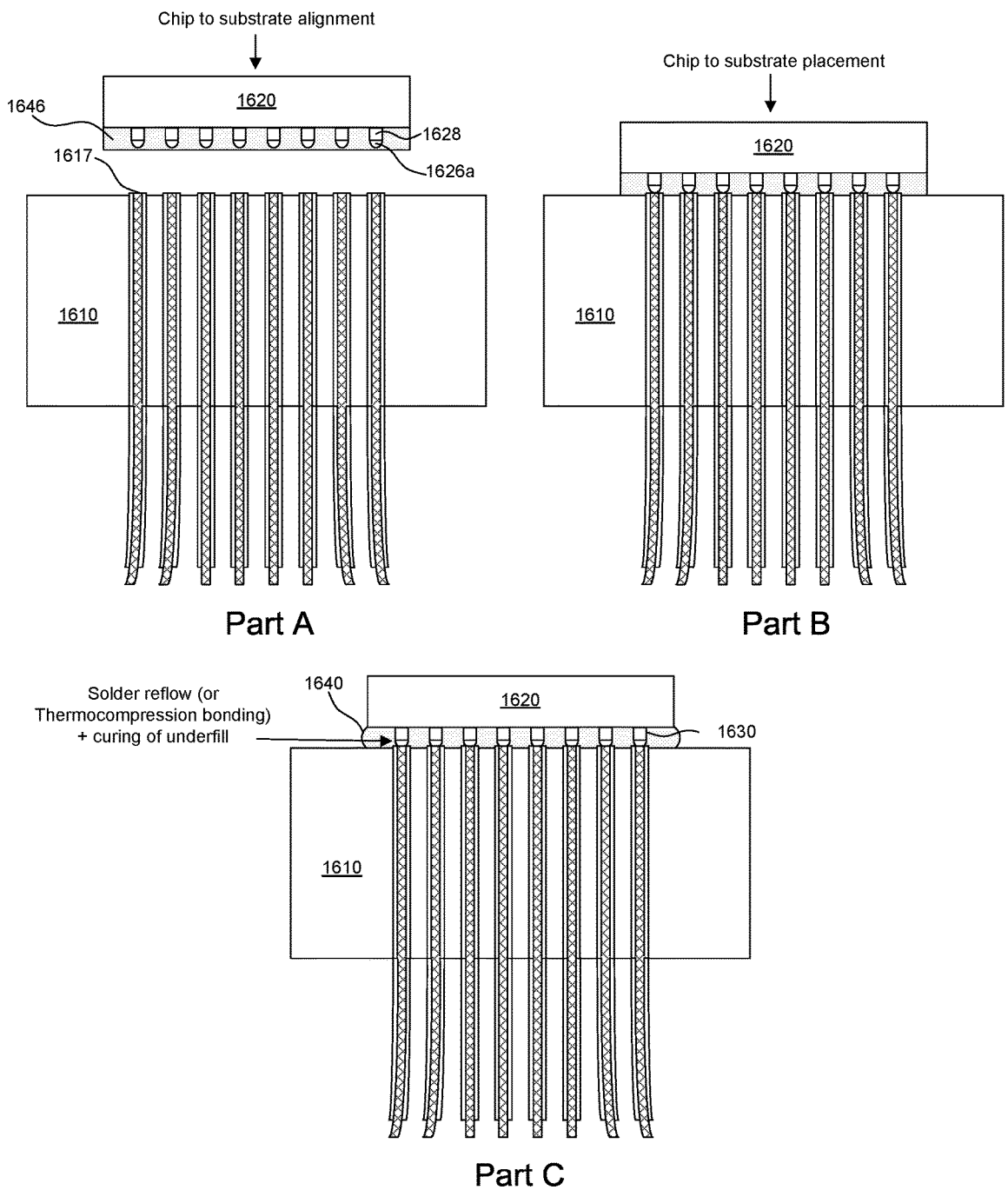
FIG. 16 Parts A, B, and C show an example of a neural-interface probe and methods of forming thereof, in accordance with various embodiments.

FIG. 16 illustrates a neural-interface probe and a method of forming the probe in accordance with some embodiments. A wire bundle substrate 1610 may comprise a plurality of connection pads 1617, similar to that shown in part A of FIG. 15. A chip 1620 comprising a plurality of conductive pillars 1628 with solder caps 1626a may be provided. The chip may further comprise a chip-level underfill 1646 embedding the solder-capped conductive pillars. The chip-level underfill may be applied, for example to the chip shown in part D of FIG. 7. In some cases, the underfill may be applied at a wafer level prior to dicing the wafer to form chip 1620.

The chip and the wire bundle substrate may be aligned, by aligning the solder-capped conductive pillars to the connection pads on the substrate (part A). After the solder-capped conductive pillars have been aligned to the connection pads, the chip is placed onto the wire bundle substrate (part B). Next, the assembly of part B undergoes a reflow process during which the solder caps (on the conductive pillars) melt and wet the connection pads on the substrate to form a plurality of interconnects 1630 (part C). In some cases, the chip may be bonded to the substrate using a thermocompression process by applying heat and pressure, instead of using a reflow process. During the reflow process (or thermocompression bonding process), the epoxy resin in the chip-level underfill cures to form underfill 1640 protecting the interconnects (part C). Accordingly, the interconnect formation and underfill curing can be performed via a single bonding process (reflow or thermocompression) in the embodiment of FIG. 16.

Figure 17:
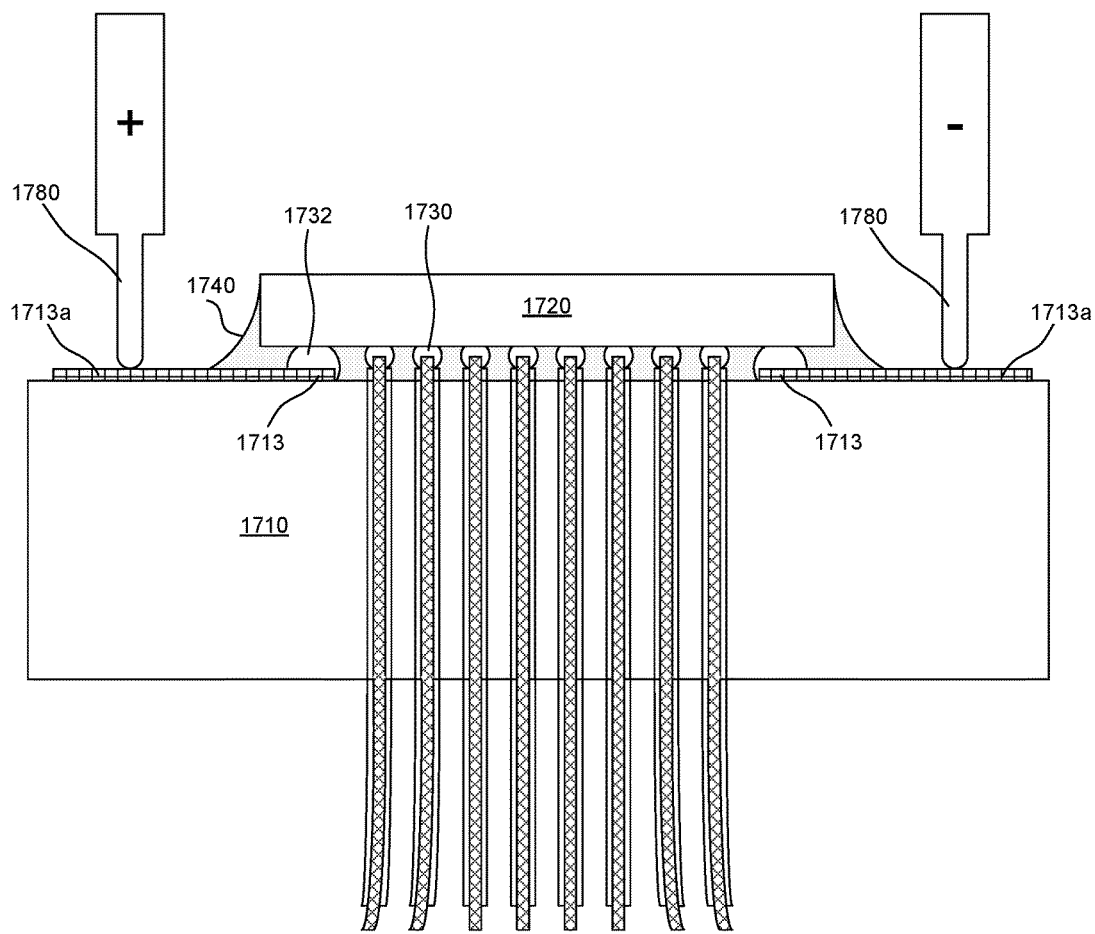
FIG. 17 shows an example of a neural-interface probe and methods of forming thereof, in accordance with various embodiments.

FIG. 17 illustrates a neural-interface probe and a method of forming the probe in accordance with some embodiments. The embodiment in FIG. 17 is similar to the embodiment in FIG. 13 except for the following differences. In FIG. 17, a wire bundle substrate 1710 may comprise alignment pads 1713. The alignment pads can be used for solder alignment of a chip 1720 to the substrate, similar to that previously described in FIG. 13. Additionally, the alignment pads may extend beyond the boundary of an underfill 1740 to form electrodes 1713a. Probes 1780 may be provided in contact with the electrodes 1713a. The probes may be connected to an external device (not shown). The external device may be configured to transmit electrical power and/or signals to the chip. The external device may also be configured to receive signals indicative of neuronal activity from the chip.

In some embodiments, the chip 1720 may include a ground reference plane. One or more wires may be connected to the ground reference plane. For example, one or more wires in the wire bundle substrate 1710 may be connected to the ground reference plane via one or more interconnects 1730 and/or 1732. Optionally, one or more external wires (that are not part of the wire bundle substrate 1710) may be directly connected to the ground reference plane via one or more bond pads on the chip 1720. The wires that are connected to the ground reference plane of the chip may be configured to extend outside of a housing encapsulating the probe, and connect to a ground electrode that is remote from the probe.

In some embodiments, a neural-interface probe may be disposed within an enclosure. The enclosure may have a low profile that allows it to occupy a low volume of space. In some embodiments, the enclosure may be a metal container having one side where the distal portion of the wires exits. For example, the enclosure may be a metal box comprising five walls surrounding the probe, and an open side where the distal portion of the wires exits. In some cases, the enclosure may also serve as a ground electrode, and one or more wires may be connected from the enclosure to a ground reference plane on a chip.

In some embodiments, one or more pixels on the chip may be connected to one or more bond pads located on a periphery of the chip. For example, one or more pixels may be connected to the bond pads corresponding to interconnects 1732. The one or more pixels may be separated from the other active pixels in the central region of the chip. Accordingly, the one or more pixels connected to the peripheral bond pads can allow for bypassing of CMOS electronics during diagnostic testing of the chip.

In some embodiments, a secondary moisture resistance structure may be provided to protect the chip in the event that the encapsulant material (e.g., underfill) cracks or ruptures. For example, the chip (including the bond pads thereon) may be completely encapsulated via thin film deposition of a dielectric layer (e.g., silicon oxide, aluminum oxide, and/or silicon nitride) or a film stack comprising different dielectrics. A thickness of the dielectric layer (or film stack) may range from about 10 nm, 20 nm, 30 nm, 40 nm, 50 nm, 60 nm, 70 nm, 80 nm, 90 nm, 100 nm, or greater than 100 nm. The dielectric layer (or film stack) may be formed by atomic layer deposition, chemical vapor deposition, sputtering, or any other deposition method. After the dielectric layer (or film stack) has been formed, the backside of the chip may optionally be planarized using chemical mechanical polishing, without removing the underlying circuitry. Subsequently, vias may be etched through the dielectric layer (or film stack) to re-expose the underlying pads. Each via may be aligned to each pad, and a diameter of each via may be smaller than the size of the corresponding pad. After the vias have been formed, a metal may be deposited into the vias. The metal may be a biocompatible metal that does not easily degrade in a moist environment. The metal may be formed as a metal stack comprising, for example an adhesion layer (Ti or Cr) and a noble metal. The dielectric layer (or film stack) may serve as a secondary moisture resistance structure that hermetically seals the chip circuitry, and that can protect the chip even when the encapsulant material fails mechanically (e.g., crack or rupture).

Figure 18A:
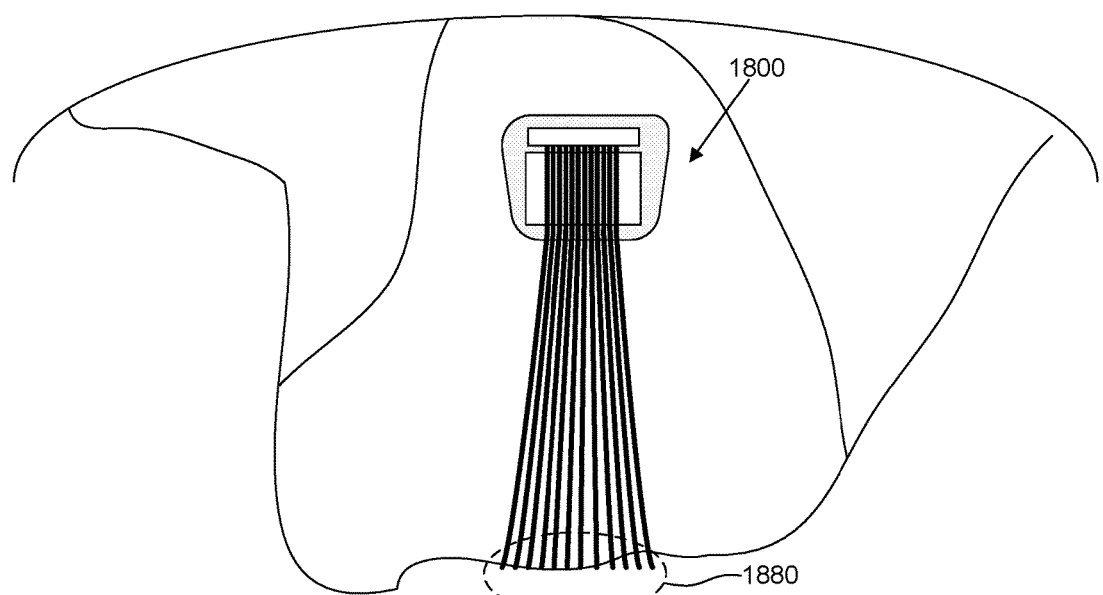
FIG. 18A depicts a schematic of a neural-interface probe implanted deep within a brain, in accordance with some embodiments.

FIG. 18A depicts a schematic of a neural-interface probe 1800 implanted deep within a brain, in accordance with some embodiments. The probe 1800 may be inserted into the deep-tissue regions of the brain of a test subject. During insertion of the probe, the free ends of the wires spread out within the brain tissue such that the electrodes deploy in a three-dimensional arrangement over a deep-brain target area 1880.

Figure 18B:
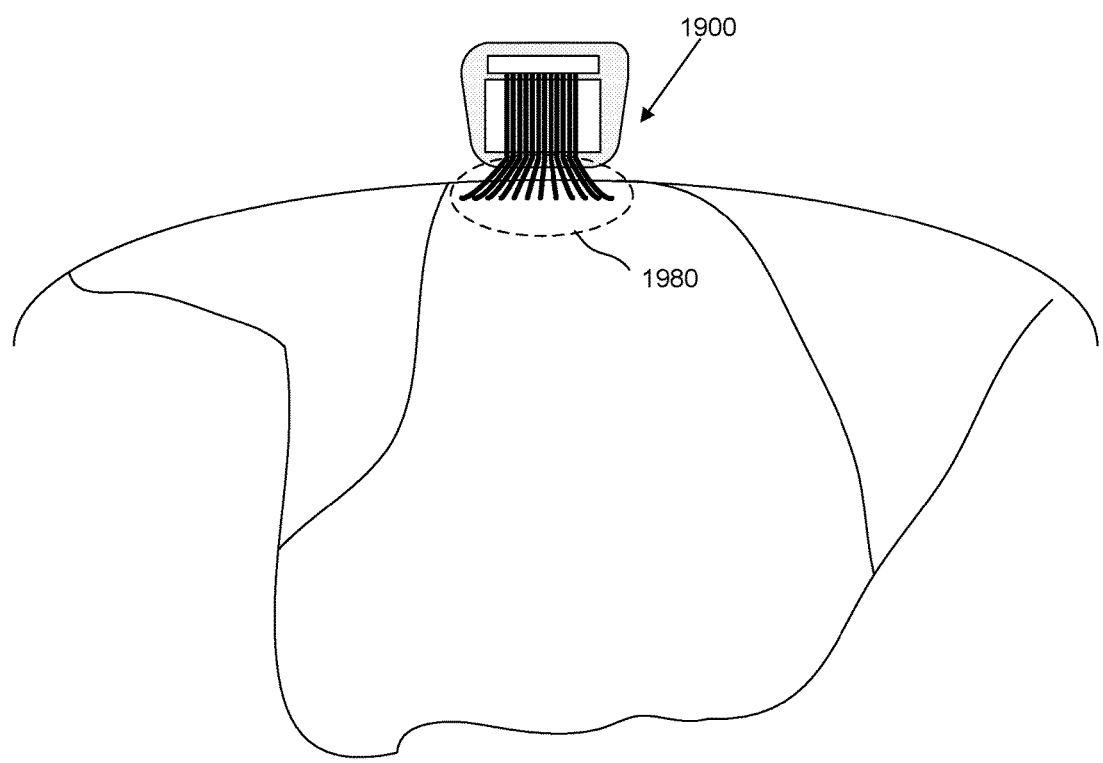
FIG. 18B depicts a schematic of a neural-interface probe implanted on a superficial target on a brain, in accordance with some embodiments.

FIG. 18B depicts a schematic of a neural-interface probe 1900 implanted on a superficial target on a brain, in accordance with some embodiments. The probe may be inserted onto a superficial tissue region 1980 of the brain of a test subject. The tissue region 1980 may, for example be a cortical region of the brain. When the probe 1900 is implanted on the tissue region 1980, the free ends of the wires spread out such that the electrodes deploy in a three-dimensional arrangement over the tissue region 1980.

Comparing FIGS. 18A and 18B, it may be observed that the neural-interface probe 1800 has a high aspect ratio since it is used in deep brain regions, whereas the neural-interface probe 1900 has a low aspect ratio since it is used in shallow or superficial brain regions. In some embodiments, a length of a neural-interface probe may range from about 1 cm to about 8 cm. Accordingly, neural-interface probes of different lengths and other dimensions (width, etc.) may be used for different regions of the brain in accordance with various embodiments of the invention. The probes in FIGS. 18A and 18B can be used to implement a method for monitoring and/or stimulating neural activity. In some embodiments, the method may comprise inserting the probe into a brain, such that the flexible distal portion of the wires interfaces and is in contact with an area of the neural matter. The method may further comprise monitoring and/or stimulating neural activity in the area via a plurality of electrical signals transmitted between the chip and the neural matter. The plurality of electrical signals may be transmitted through the plurality of wires. In some embodiments, the method may further comprise transmitting the electrical signals from the probe to an external monitoring device via one or more wireless or wired communication channels.

In some embodiments, the implanted neural-interface probes may be connected to the external world via a percutaneous wire. The percutaneous wire may be inserted through a patient's scalp. In other embodiments, the implanted neural-interface probes may be connected to the external world via a wireless telemetry unit.

In some embodiments, an encapsulant material may be disposed surrounding the chip. The encapsulant material may have asymmetrical thicknesses above, below, and/or around the chip, so as to dissipate heat (that is generated by the chip) away from the brain. In some cases, different parts of the encapsulant material may have different thermal conductivities. For example, a portion of the encapsulant material above the chip (further away from the brain) may have a higher thermal conductivity, and another portion of the encapsulant material below the chip (closer to the brain) may have a lower thermal conductivity, to thereby promote heat dissipation away from the brain.

In some embodiments, a backside of the chip may be bonded to a heatsink foil (or heat spreader). The heatsink foil may have a larger surface area than the chip. The heatsink foil may or may not be encapsulated in the encapsulant material.

In some embodiment, the chip and the wire bundle may be disposed beneath the skull (i.e., within the skull). In other embodiments, the chip may be recessed into the skull to reduce volume displacement in the intracranial space. In some further embodiments, the chip may be disposed outside of the skull but under the scalp, and the wire bundle (e.g., the distal portion of the wires) may pass through a hole in the skull. In some embodiments, the chip and the wire bundle may be disposed outside the scalp, and the wire bundle may pass through the scalp and the skull.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A neural-interface probe comprising:
a chip comprising a plurality of bond pads;
a wire bundle substrate comprising a plurality of wires extending through said substrate, wherein the plurality of wires comprises: (1) a proximal portion connected to the plurality of bond pads to thereby couple the chip to said substrate, and (2) a flexible distal portion configured to interface with neural matter, wherein the proximal portion of the plurality of wires is connected to the plurality of bond pads via a plurality of interconnects comprising solder formed between the chip and the wire bundle substrate; and
a housing formed by overmolding an epoxy block around the chip and the wire bundle substrate, wherein the housing is configured to seal the chip and substrate by entirely disposing the chip and the substrate within the epoxy block.

2. The probe of claim 1, wherein the proximal portion of the wires extends from a first surface of the substrate, and the distal portion of the wires extends from a second surface of the substrate that is different from the first surface.

3. The probe of claim 1, wherein the flexible distal portion of the wires is configured to substantially conform to a surface of the neural matter when said distal portion is in contact with the surface of the neural matter.

4. The probe of claim 3, wherein the flexible distal portion of the wires is configured to bend to substantially conform to the surface of the neural matter, wherein said surface of the neural matter corresponds to a cortical layer of interest.

5. The probe of claim 3, wherein the flexible distal portion of the wires is configured to partially penetrate the surface of the neural matter.

6. The probe of claim 1, wherein the plurality of wires each has an aspect ratio greater than 500:1 in a longitudinal direction extending through the substrate, and wherein the distal portion of the plurality of wires has a same length or different lengths.

7. The probe of claim 1, wherein the plurality of bond pads occupy at least 50% of a total surface area of the plurality of pixels of the chip.

8. The probe of claim 7, wherein the plurality of interconnects are configured to electrically connect the plurality of wires to the chip.

9. The probe of claim 7, wherein the plurality of interconnects are formed by aligning and joining the proximal portion of the plurality of wires to the plurality of bond pads.

10. The probe of claim 9, wherein the plurality of interconnects are formed by aligning the proximal portion of the plurality of wires to the plurality of bond pads to a precision within 10 µm.

11. The probe of claim 7, wherein the chip is rigidly coupled to the substrate via the plurality of interconnects and the housing.

12. The probe of claim 7, wherein the chip is not configured to be detachable from the substrate without damaging or breaking one or more of the interconnects.

13. The probe of claim 1, wherein the flexible distal portion of the plurality of wires extends outside of the housing, and the proximal portion of the plurality of wires is disposed within the housing.

14. The probe of claim 1, wherein the housing is configured to hermetically seal the chip and the substrate.

15. The probe of claim 1, wherein the housing is configured to provide structural rigidity to the probe along a longitudinal direction that is substantially parallel to the plurality of wires.

16. The probe of claim 1, wherein the plurality of wires are (1) randomly distributed at different pitches in the substrate, or (2) uniformly distributed at a same pitch in the substrate.

17. The probe of claim 1, wherein the proximal portion of one or more wires is connected to one or more bond pads.

18. The probe of claim 1, wherein the flexible distal portion of the wires is configured to spread out in a plurality of different directions in a three-dimensional configuration.

19. The probe of claim 1, wherein a diameter of each of the plurality of wires ranges from about 5 nm to about 25 µm, and wherein a length of the flexible distal portion of the wires ranges from about 2 mm to about 4 cm.

20. The probe of claim 1, wherein the chip further comprises a protrusion formed on each of the plurality of bond pads to increase a stand-off height between the chip and the wire bundle substrate, wherein the protrusion comprises a conductive pillar having a solder cap formed on an end portion of the conductive pillar.

21. The probe of claim 1, wherein each of the plurality of wires comprises a conductive core, wherein the conductive core of each wire in the first set of wires is surrounded by an insulating layer, and wherein the conductive core of each wire in the second set of wires is not surrounded by an insulating layer.

22. A method for forming a neural-interface probe, said method comprising:
providing a chip that comprises a plurality of bond;
providing a wire bundle substrate that comprises a plurality of wires extending through said substrate, wherein the plurality of wires comprises: (1) a proximal portion configured to be connected to the plurality of bond pads to thereby couple the chip to said substrate, and (2) a flexible distal portion configured to interface with neural matter;
attaching the chip to the wire bundle substrate by connecting the proximal portion of the wires to the plurality of bond pads via a plurality of interconnects comprising solder formed between the chip and the wire bundle substrate; and
overmolding a housing by providing an epoxy block entirely surrounding the chip and the wire bundle substrate to seal the chip and substrate.

23. A method for monitoring and/or stimulating neural activity, the method comprising:
inserting the probe of claim 1 into a brain, such that the flexible distal portion of the wires interfaces and is in contact with an area of the neural matter; and
monitoring and/or stimulating neural activity in said area via a plurality of electrical signals transmitted between the chip and the neural matter through the plurality of wires.

24. The method of claim 23, further comprising: transmitting the electrical signals from the probe to an external monitoring device via one or more wireless or wired communication channels.

* * * * *